(12) United States Patent
Tan et al.

(10) Patent No.: US 11,078,250 B2
(45) Date of Patent: Aug. 3, 2021

(54) HIGH-ACTIVITY LONG-ACTING HYPOGLYCEMIC FUSION PROTEIN AS WELL AS PREPARATION METHOD AND MEDICAL APPLICATION THEREOF

(71) Applicant: China Pharmaceutical University, Nanjing (CN)

(72) Inventors: Shuhua Tan, Nanjing (CN); Lili Gu, Nanjing (CN); Jian Fu, Nanjing (CN); Yongbo Zhang, Nanjing (CN); Qinghua Tian, Nanjing (CN); Yue Wang, Nanjing (CN); Xiaojian Gong, Nanjing (CN)

(73) Assignee: China Pharmaceutical University, Nanjing (CN)

( * ) Notice: Subject to any disclaimer, the term of this patent is extended or adjusted under 35 U.S.C. 154(b) by 0 days.

(21) Appl. No.: 16/278,094

(22) Filed: Feb. 16, 2019

(65) Prior Publication Data
US 2019/0322717 A1 Oct. 24, 2019

Related U.S. Application Data

(63) Continuation of application No. PCT/CN2017/093699, filed on Jul. 20, 2017.

(30) Foreign Application Priority Data

Aug. 16, 2016 (CN) .......................... 201610678121.0

(51) Int. Cl.
| | | |
|---|---|---|
| *A61K 38/26* | (2006.01) | |
| *C07K 14/575* | (2006.01) | |
| *A61P 3/08* | (2006.01) | |
| *A61K 38/22* | (2006.01) | |
| *C12N 15/70* | (2006.01) | |
| *C07K 14/605* | (2006.01) | |

(52) U.S. Cl.
CPC ........ *C07K 14/57563* (2013.01); *A61K 38/22* (2013.01); *A61P 3/08* (2018.01); *C12N 15/70* (2013.01); *C07K 14/605* (2013.01)

(58) Field of Classification Search
CPC .......................... C07K 14/605; C07K 2319/30
See application file for complete search history.

(56) References Cited

U.S. PATENT DOCUMENTS

| 6,924,264 B1 * | 8/2005 | Prickett ..................... A61P 3/10 |
| | | 514/6.9 |
| 9,580,509 B2 * | 2/2017 | Dimasi .............. C07K 16/1214 |
| 2004/0053370 A1 | 3/2004 | Glaesner et al. |
| 2005/0186662 A1 | 8/2005 | Low |
| 2013/0142795 A1 | 6/2013 | Bai et al. |

FOREIGN PATENT DOCUMENTS

| CN | 102311501 A | 1/2012 |
| CN | 102453094 A | 5/2012 |
| CN | 102952192 A | 5/2012 |
| CN | 102558362 A | 7/2013 |
| CN | 105753963 A | 7/2016 |
| CN | 106046176 A | 10/2016 |

OTHER PUBLICATIONS

Internation Search Report of PCT/CN2017/093699, dated Sep. 28, 2017.

\* cited by examiner

*Primary Examiner* — Gyan Chandra
(74) *Attorney, Agent, or Firm* — True Shepherd LLC; Andrew C. Cheng

(57) ABSTRACT

The disclosure provides a high-activity long-acting hypoglycemic fusion protein, which is formed by connecting, via a linker peptide or directly, a high-activity Exendin-4 mutant with an optimally mutated Fc fragment of a human immunoglobulin IgG1. The optimally mutated Fc fragment of the human immunoglobulin IgG1 comprises an optimally mutated human IgG1 hinge region and human IgG1 constant regions CH2 and CH3.

7 Claims, 10 Drawing Sheets

Specification includes a Sequence Listing.

A

B

A

B

A

B

HIGH-ACTIVITY LONG-ACTING HYPOGLYCEMIC FUSION PROTEIN AS WELL AS PREPARATION METHOD AND MEDICAL APPLICATION THEREOF

CROSS-REFERENCE TO RELATED APPLICATIONS

This application is a continuation of International Patent Application No. PCT/CN2017/093699 with a filing date of Jul. 20, 2017, designating the United States, and further claims priority to Chinese Patent Application No. 201610678121.0 with a filing date of Aug. 16, 2016. The content of the aforementioned applications, including any intervening amendments thereto, are incorporated herein by reference.

TECHNICAL FIELD

The disclosure belongs to the field of biopharmaceuticals, and particularly relates to a high-activity long-acting hypoglycemic fusion protein and application thereof in preparation of a drug for treating diabetes mellitus.

BACKGROUND OF THE PRESENT INVENTION

Diabetes mellitus (DM), commonly referred to as diabetes, is a group of metabolic disorders in which there are high blood sugar levels. DM results from the pancreas's failure to produce enough insulin and/or insulin resistance. There are two main types of DM: type 1 DM and type 2 DM in which type 2 DM makes up 90%-95% of the cases. Type 2 DM was previously referred to as "non-insulin-dependent diabetes mellitus" (NIDDM), which begins with a pathological condition in which tissues fail to response normally to insulin (insulin resistance) and with the pancreas' failure to produce enough insulin due to significant hypoinsulinsim. In type 2 DM, there are high blood sugar levels over a prolonged period. If left untreated, diabetes can cause many acute complications.

Drugs for treating type 2 DM mainly include sulfonylureas, biguanides, Nateglinide, thiazolidinediones, α-glucosidase inhibitor, dipeptidyl peptidase IV (DPP-4) inhibitor, glucagon-like peptide-1 (GLP-1) receptor agonist, sodium-glucose co-transport protein 2 (SGLT-2) inhibitor and the like. DPP-4 inhibitor and GLP-1 receptor agonist can protect various systems such as digestion system, central nervous system and cardiovascular system in addition to the advantages of hypoglycemic activity without leading to hypoglycemia, high safety and good tolerability, etc.

Glucagon-like peptide-1 (GLP-1) is an important endogenous incretin, which is synthesized and secreted by small intestine Langerhans cells. When binding to a GLP-1 receptor, it stimulates pancreatic islet beta cells to secrete insulin, inhibits the secretion of glucagon and enhances the sensitivity of tissues to insulin, thereby reducing the concentration of blood glucose. However, GLP-1 is extremely easily degraded by DPP-4 after entering blood, with a half-life period of less than 2 min (Vilsboll T. *J Clin Endocrinol Metab.* 2003; 88: 220-4). DPP-4 is a serine protease, which can specifically cleave a dipeptide from the N terminus of GLP-1 to inactivate GLP-1.

Exendin-4 is an exogenous GLP-1 receptor polypeptide agonist found in saliva of Heloderma suspectum in northwest North America, consists of 39 amino acids, and has about 53% homology to amino acid sequence of GLP-1. The physiological function of Exendin-4 in mammals is similar to that of GLP-1, and Exendin-4 is capable of stimulating the secretion of glucose-dependent insulin, namely, it can function only when the concentration of blood glucose in an organism is high, and does not function when blood glucose is normal or low.

Exendin-4 was developed and marketed by Amylin and Eli Lily Company in America in April, 2005, and marketed in China in August, 2009 as the first GLP-1 receptor agonist drug. Exendin-4 is insensitive to DPP-4, and thus compared with GLP-1, its in-vivo half-life period is significantly increased and reaches 3.3~4 hours (Barnett A H. *Drugs Today (Barc).* 2005; 41: 563-78; Kolterman O G. *Am J Health Syst Pharm.* 2005; 62: 173-81). Exendin-4 can effectively control the concentration of blood glucose of type 2 DM patients after combined with sulfonylurea drugs, melbine or thiazolidinedione drugs in clinic. Exendin-4 has good safety and tolerance in vivo, hardly leads to hypoglycemia, and has become a first-line treatment drug for treating type 2 diabetics. However, it has the defect of high medication frequency, and needs to be injected for a patient no less than twice a day.

Exendin-4 is an exogenous GLP-1 receptor agonist peptide, its molecular structure and an interaction relationship between Exendin-4 and a GLP-1 receptor have been clearly studied (Doyle M E. *Regul Pept.* 2003; 114: 153-8; Al-Sabah S. *Br J Pharmacol.* 2003; 140: 339-46; Donnelly D. *Br J Pharmacol.* 2012; 166: 27-41). The N terminal of Exendin-4 is a random coil, $7^{th}$-$28^{th}$ amino acid residues form α helix, the C terminal is an irregular hydrophilic fragment, the N terminal is a key region for activating a receptor signal transduction pathway, and a middle position and the C terminal are receptor binding regions. Thus, based on the study on the molecular structure of Exendin-4 and the interaction relationship between Exendin-4 and GLP-1, it is possible to obtain an Exendin-4 mutant which possesses better pharmacologically activity by further optimizing the structure of Exendin-4.

Immunoglobulin IgG is one of the richest proteins in blood, and its in-vivo half-life period can be up to 21 days. Thus, in the field of biopharmaceuticals, a human IgG Fc fragment (namely, a hinge region and constant regions CH2-CH3 of human IgG) has been used to be fused with other active proteins or polypeptides to extend the in-vivo half-life period, thereby reducing medication frequency and improving dependence and tolerance of a patient on drug treatment. For example, Romiplostim developed and marketed by Amgen Company in America is a fusion protein consisting of thrombopoietin (TPO) receptor binding peptide and IgG1Fc, which not only maintains original functions in binding and activating TPO receptor to increase thrombocytopoiesis but also greatly extends its in-vivo half-life period, and is used for treating chronic immune thrombocytopenic purpura (ITP) in clinic. As another example, for PTH-Fc, Trebananib (Amg386), AMG819 and the like, the peptides are fused with the Fc fragment of human IgG to extend the in-vivo half-life period of the polypeptide drugs (Kostenuik P J. *J Bone Miner Res.* 2007; 22:1534-47; Shimamoto G. *MAbs.* 2012; 4:586-91). Since mammalian cell expression system is high in expression cost, long in culture period and difficult in process scaling-up, the above Fc fusion proteins are prepared by using *E. coli* expression system. Compared to mammalian cell expression system, *E. coli* expression has significant advantages of homogeneity of the product, no galactosylated modification, short ferment cycle and low cost (Shimamoto G. *MAbs.* 2012; 4:586-91), (Kostenuik P J. *J Bone Miner*

*Res.* 2007; 22: 1534-47; Shimamoto G. *MAbs.* 2012; 4: 586-91). However, since the fusion proteins usually form inclusion bodies when expressed in *E. coli*, the downstream process for the denaturation and renaturation of inclusion body to obtain active soluble proteins is complicated, which eventually brings large difficulty to preparation of samples (Kostenuik P J. *J Bone Miner Res.* 2007; 22: 1534-47; Shimamoto G. *MAbs.* 2012; 4: 586-91; Baneyx F. *Nat Biotechnol.* 2004; 22: 1399-408).

SUMMARY OF PRESENT INVENTION

In order to overcome the defects in the prior art, the disclosure provides a high-activity long-acting hypoglycemic fusion protein modified by using an optimally mutated Fc fragment of human immunoglobulin IgG1. The fusion protein is formed by connecting, by a linker peptide or directly, Exendin-4 or a high-activity Exendin-4 mutant thereof with an optimally mutated Fc fragment of human immunoglobulin IgG1. The fusion protein of the disclosure not only has high-activity long-acting hypoglycemic effect but also can be expressed in *E. coli* in a soluble form, and the soluble expression product can be directly separated and purified from the supernatant of bacterial lysate, thereby greatly simplifying a production and preparation process, improving product yield and reducing production cost.

The specific technical solutions of the disclosure are as follows:

A high-activity long-acting hypoglycemic fusion protein is formed by connecting, via a linker peptide or directly, a high-activity Exendin-4 mutant with an optimally mutated Fc fragment of a human immunoglobulin IgG1, the Fc fragment comprises an optimally mutated human IgG1 hinge region and human IgG1 constant regions CH2 and CH3, and the amino acid sequence of the optimally mutated human IgG1 hinge region (hereinafter "mhIgG1 hinge region") is -SGGGGSDKTHTCPPCP- (SEQ ID NO: 6) and is formed by mutating an original sequence -VEPKSCDKTHTCPPCP- (SEQ ID NO: 5) of a natural human IgG1 hinge region (hereinafter "nhIgG1 hinge region). The sequence of the human IgG1 constant regions CH2 and CH3 is as shown in SEQ ID NO: 7.

The above linker peptide is a flexible peptide rich in Gly and/or Ala and/or Ser, having 1~50 amino acid residues in length, and the amino acid sequence of a preferred linker peptide is as shown in SEQ ID NO: 8.

The high-activity Exendin-4 mutants are formed by mutating Leu at the $21^{st}$ position of wild Exendin-4 (SEQ ID NO: 1) into Lys (EX-L21K, SEQ ID NO: 2), Arg (SEQ ID NO: 3) or His (SEQ ID NO: 4).

In a preferred solution of the disclosure, the fusion protein comprises a pharmacological activity-enhanced Exendin-4 mutant EX-L221K, a linker peptide rich in Gly, an optimally mhIgG1 hinge region and human IgG1 constant regions CH2 and CH3. The fusion protein is called EX-L21K-mhIgG1Fc for short, and its amino acid sequence is as shown in SEQ ID NO: 11.

In another preferred solution of the disclosure, the fusion protein comprises wild Exendin-4, a linker peptide rich in Gly, an optimally mhIgG1 hinge region and human IgG1 constant regions CH2 and CH3. The fusion protein is called EX-mhIgG1Fc for short, and the amino acid sequence of the protein is as shown in SEQ ID NO: 9.

The optimally mhIgG1 hinge region -SGGGGSDKTHTCPPCP- (SEQ ID NO: 6) is formed by mutating the original sequence -VEPKSCDKTHTCPPCP- (SEQ ID NO: 5) of an nmIgG1 hinge region. The N terminal of the mhIgG1 hinge region is rich in Gly and Ser, which not only enhances the flexibility and hydrophilia of the N terminal of the hinge region and is beneficial to maintain the biological activity and solubility of the fusion protein, but also eliminates a possibility that the first Cys at the N terminal of the original hinge region forms a mispairing disulfide bond during the protein expression.

Another objective of the disclosure is to provide a preparation method of the above high-activity long-acting hypoglycemic fusion protein, comprising the following steps:

(1) designing to synthesis and clone a coding gene of the fusion protein;

(2) constructing as an expression plasmid to be transformed into an *E. coli* host cell for soluble expression; and (3) collecting bacterial sludge and broken walls, collecting broken wall supernatant, and separating and purifying to obtain the soluble fusion protein as described in the disclosure.

The lasting time of the in-vivo hypoglycemic activity and hypoglycemic effect of the long-acting fusion proteins EX-mhIgG1Fc and EX-L21K-mhIgG1Fc of the disclosure is significantly superior to that of wild Exendin-4, and the effect of EX-L21K-mhIgG1Fc is more superior.

Another objective of the disclosure is to provide application of the high-activity long-acting hypoglycemic fusion protein of the disclosure in preparation of a drug for reducing blood glucose.

The long-acting fusion proteins EX-mhIgG1Fc and EX-L21K-mhIgG1Fc of the disclosure can be expressed in *E. coli* in a soluble form, and the expression product exists in a form of soluble dimer and can be directly separated and purified from broken wall supernatant of *E. coli*, thereby avoiding complicated downstream denaturation and renaturation treatment processes brought due to formation of inclusion bodies. However, the fusion protein consisting of wild Exendin-4 and nhIgG1Fc is expressed in *E. coli* in a form of an inclusion body, which cannot avoid the complicated downstream denaturation and renaturation treatment processes.

The long-acting fusion proteins EX-mhIgG1Fc and EX-L21K-mhIgG1Fc of the disclosure have significant advantages of high hypoglycemic activity and long hypoglycemic effecting time, which will be beneficial to reduce medication dosage for obtaining treatment effects, reduce administration frequency and improve compliance of drug treatment. They can be used for treating diabetics and other diseases benefited by reducing blood glucose.

DESCRIPTION OF THE DRAWINGS

FIG. 3 shows that A: a structural diagram of a long-acting fusion protein EX-hIgG1Fc of wild Exendin-4, which mainly comprises an initial methionine Met, wild Exendin-4, a liner peptide (-GGGG-, SEQ ID NO: 8), a nhIgG1 hinge region and constant regions CH2 and CH3; and B: a complete amino acid sequence of EX-hIgG1Fc and an artificially synthesized gene sequence thereof, wherein a shadow represents a wild Exendin-4 portion, an underline represents the nhIgG1 hinge region, and an asterisk represents a stop codon.

As shown in FIG. 10, the glucose area under the curve during 0-180 is represented by $AUC_{0\text{-}180\ min}$, ### represents $p<0.0001$ as compared with normal group; **** represent $p<0.0001$ as compared with model group (n=8, means±SEM).

DETAILED DESCRIPTION OF PREFERRED EMBODIMENTS

Specific steps of the disclosure will be illustrated through examples below, but are not limited thereto.

The terms used in the disclosure generally have their ordinary meanings in the art, unless otherwise stated.

The disclosure will be further described in detail in combination with embodiments and with reference to data in the following. It should be understood that these embodiments are only for illustrating the disclosure as examples but not limiting the scope of the disclosure in any manners.

In the following examples, various processes and methods that are not described in detail are well-known conventional methods in the art.

The disclosure will be illustrated in combination with embodiments in the following.

All of materials, reagents and the like used in the following examples, unless otherwise specified herein, are commercially available.

Example 1 Design of a Long-Acting Fusion Protein of Wild Exendin-4 and a Long-Acting Fusion Protein of a High-Activity Exendin-4 Mutant 1. The amino acid sequence (SEQ ID NO: 1) of wild Exendin-4, and Leu at the 21$^{st}$ position is mutated into Lys to obtain the amino acid sequence (SEQ ID NO: 2) of the high-activity Exendin-4 mutant (EX-L21K).

The amino acid sequence of wild Exendin-4:

(SEQ ID NO: 1)
HGEGTFTSDLSKQMEEEAVRLFIEWLKNGGPSSGAPPPS.

The amino acid sequence (SEQ ID NO: 2) of a high-activity Exendin-4 mutant (EX-L21K): HGEGTFTSDLSKQMEEEAVRKFIEWLKNGGPSSGAPPPS (SEQ ID NO: 2).

2. The amino acid sequence of an optimally mhIgG1 hinge region is seen in SEQ ID NO: 6, which is mutated by a nhIgG1 hinge region (the amino acid sequence is seen in SEQ ID NO: 5) (Edelman G M. *Proc Natl Acad Sci USA*. 1969; 63: 78-85). Compared with the nhIgG1 hinge region, amino acid at the N terminal region of the mhIgG1 hinge region is rich in Gly and Ser, so that the flexibility and hydrophilia of the N terminal of the hinge region are enhanced, a possibility that the first Cys at the N terminal of the original hinge region forms a mispairing disulfide bond during the protein expression is eliminated. The underline portion is a mutation region.

The amino acid sequence of the nhIgG1 hinge region (hIgG1 hinge region):

(SEQ. ID NO: 5)
VEPKSCDKTHTCPPCP.

The amino acid sequence of the optimally mutated human hIgG1 hinge region (mutated human IgG1 hinge, called mhIgG1 hinge region for short):

(SEQ. ID NO: 6)
SGGGGSDKTHTCPPCP.

Design of a linker peptide sequence: the linker peptide is a flexible peptide rich in Gly and/or Ala and/or Ser, and has 1~50 amino acid residues in length, and the amino acid sequence of the preferred linker peptide is as shown in SEQ ID NO: 8.

Figure 1:
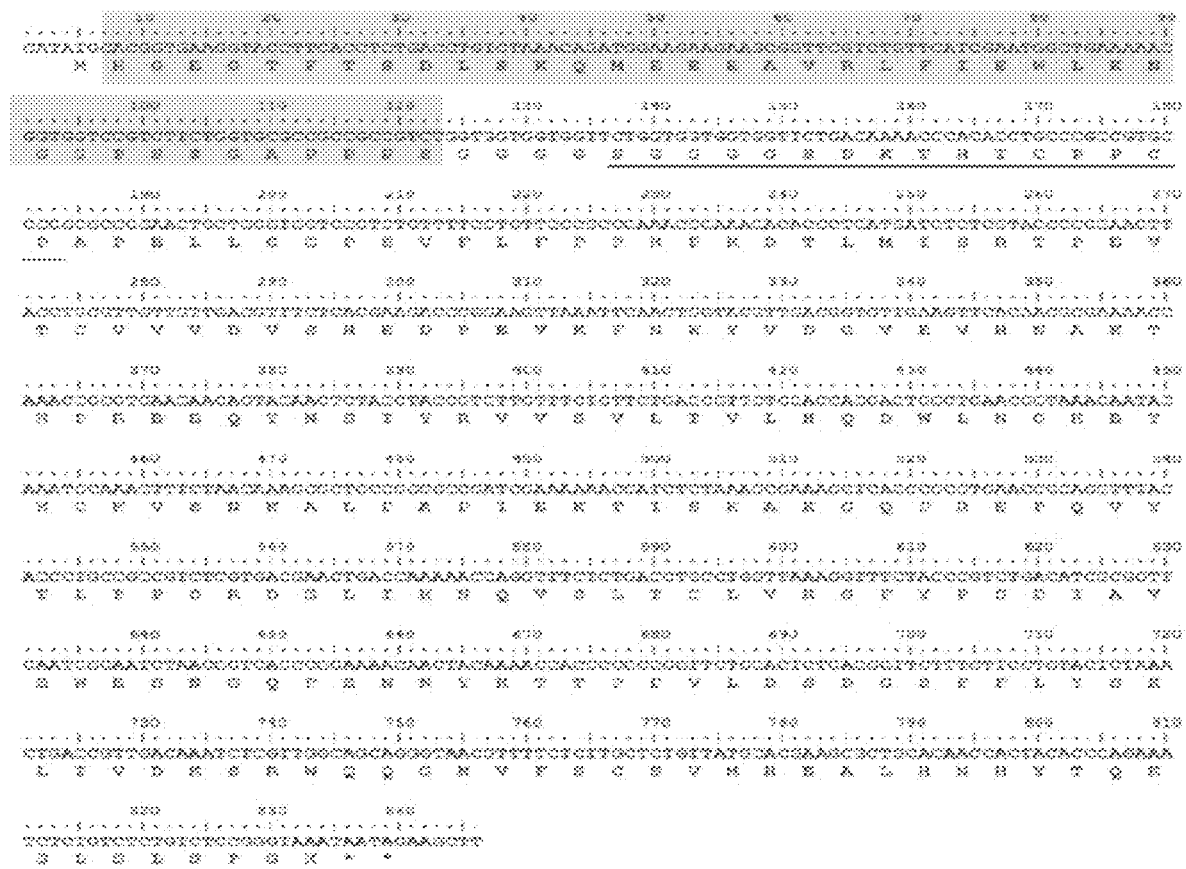
FIG. 1 is a structural diagram of a high-activity long-acting hypoglycemic fusion protein EX-mhIgG1Fc according to the disclosure. (A: a structural diagram of long-acting fusion protein EX-mhIgG1Fc of wild Exendin-4, which mainly includes an initial methionine Met, wild Exendin-4, a liner peptide (-GGGG-, SEQ ID NO: 8), an optimally mhIgG1 hinge region, constant regions CH2 and CH3. B: a complete amino acid sequence of EX-mhIgG1Fc and an artificially synthesized gene sequence thereof, wherein a shadow represents a wild Exendin-4 (SEQ ID NO: 1), an underline represents the optimally mhIgG1 hinge region (SEQ ID NO: 6), and an asterisk represents a stop codon.

3. The long-acting fusion protein EX-mhIgG1Fc of wild Exendin-4 consists of the following parts: wild Exendin-4, a linker peptide, and an optimally mhIgG1 hinge region and constant regions CH2 and CH3 of human IgG1. Its structure diagram is seen in FIG. 1 (shown in part A), and its amino acid sequence (SEQ ID NO: 9) and a coding gene sequence (SEQ ID NO: 10) designed according to codons preferred by *E. coli* is seen in FIG. 1 (shown in part B).

Figure 2:
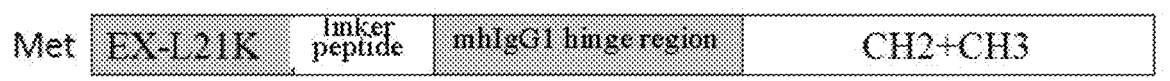
FIG. 2 is a structural diagram of a high-activity long-acting hypoglycemic fusion protein EX-L21K-mhIgG1Fc according to the disclosure. (A: a structural diagram of a long-acting fusion protein EX-L21K-mhIG1Fc of high-activity Exendin-4 mutant (EX-L21K), which mainly comprises initial methionine Met, high-activity Exendin-4, a high-activity Exendin-4 mutant (EX-L21K), a linker peptide (-GGGG-, SEQ ID NO: 8), mhIgG1 hinge region and constant regions CH2 and CH3. B: a complete amino acid sequence of EX-L21K-mhIgG1Fc and an artificially synthesized gene sequence thereof, wherein a shadow represents a high-activity Exendin-4 mutant (EX-L21K, SEQ ID NO: 2), an underline represents the optimally mhIgG1 hinge region (SEQ ID NO: 6), and an asterisk represents a stop codon.
Figure 2:
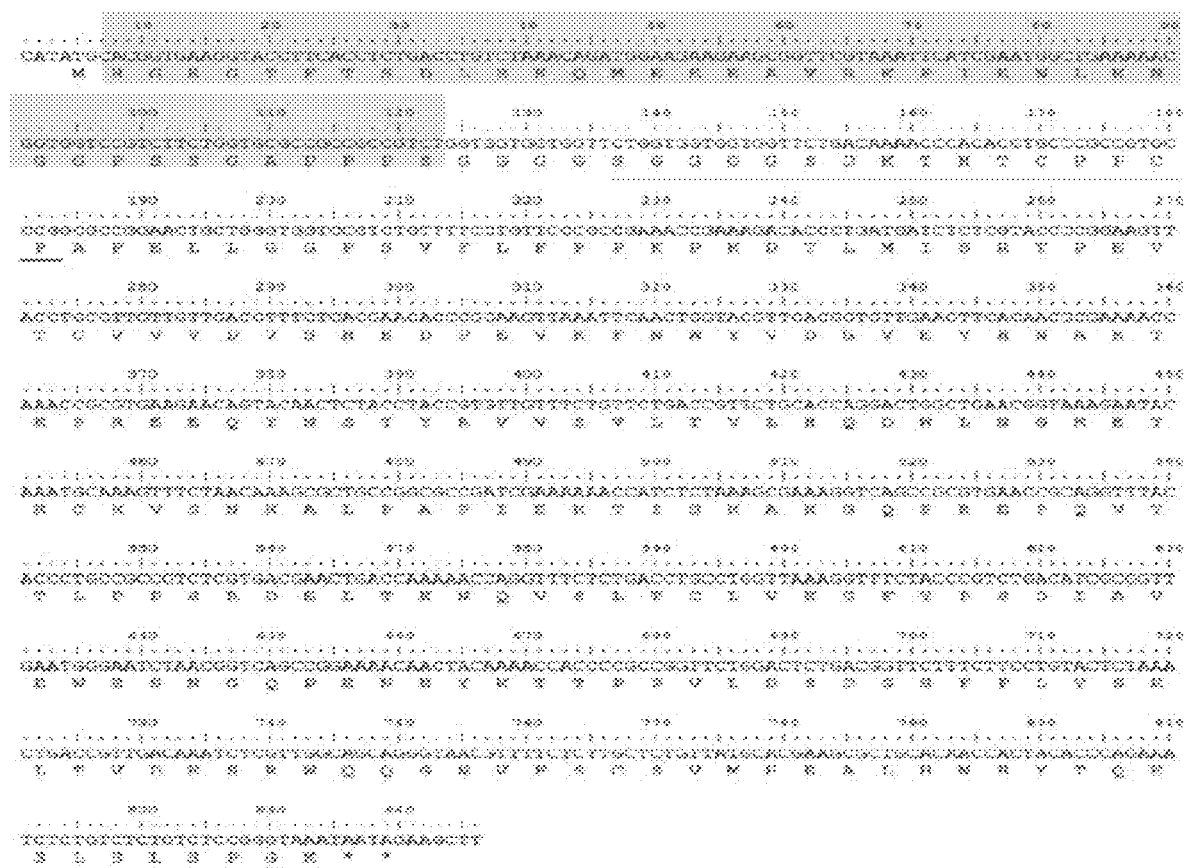

4. The long-acting fusion protein EX-L21K-mhIgG1Fc of the high-activity Exendin-4 mutant EX-L21K consists of the following parts: a high-activity Exendin-4 mutant EX-L21K, a linker peptide, and a mhIgG1 hinge region and constant regions CH2 and CH3 of an optimally mhIgG1. Its structure diagram is seen in FIG. 2 (shown in part A), and its amino acid sequence (SEQ ID NO: 11) and a coding gene sequence (SEQ ID NO: 12) designed according to codons preferred by *E. coli* is seen in FIG. 2 (shown in part B).

Figure 3:
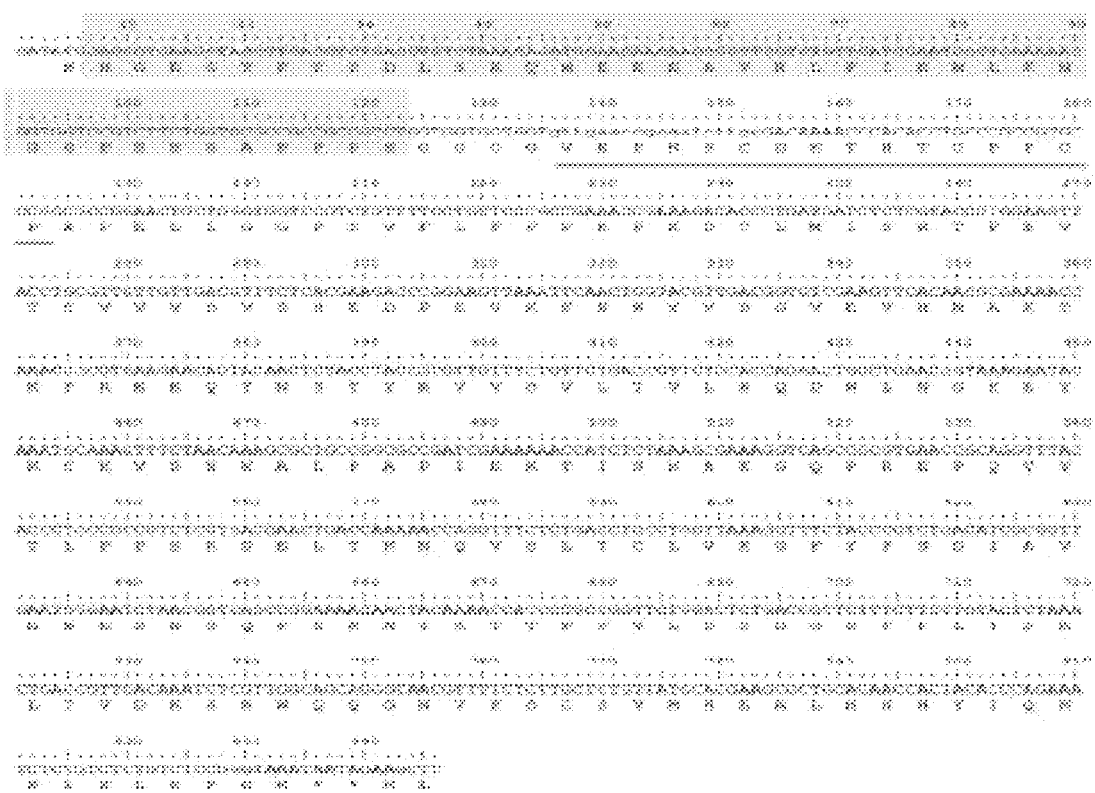
FIG. 3 shows that A: a structural diagram of a long-acting fusion protein EX-hIgG1Fc of wild Exendin-4, which mainly comprises an initial methionine Met, wild Exendin-4, a liner peptide (-GGGG-, SEQ ID NO: 8), a nhIgG1 hinge region and constant regions CH2 and CH3; and B: a complete amino acid sequence of EX-hIgG1Fc and an artificially synthesized gene sequence thereof, wherein a shadow represents a wild Exendin-4 portion (SEQ ID NO: 1), an underline represents the nhIgG1 hinge region (SEQ ID NO: 5), and an asterisk represents a stop codon.

5. The long-acting fusion protein EX-hIgG1Fc of wild Exendin-4 consists of the following parts: wild Exendin-4, a linker peptide, and a nhIgG1 hinge region and constant regions CH2 and CH3 of nhIgG1. Its structure diagram is seen in FIG. 3 (shown in part A), and its amino acid sequence (SEQ ID NO: 13) and a coding gene sequence (SEQ ID NO: 14) designed according to codons preferred by *E. coli* is seen in FIG. 3 (shown in part B).

Example 2 Cloning and Expression of a Long-Acting Fusion Protein EX-mhIgG1Fc of Wild Exendin-4

The coding gene (SEQ ID NO: 10) of the long-acting fusion protein EX-mhIgG1Fc of wild Exendin-4 is synthesized and cloned by Nanjing GenScript Biotech Co., Ltd. The gene is subjected to double-enzyme digestion with Nde I and Hind III and then sub-cloned to a prokaryotic expression vector pET21b to construct an expression plasmid pET-EX-mhIgG1Fc (shown in part A of FIG. 4), and the expression plasmid pET-EX-mhIgG1Fc is sequenced to verify the correctness of its sequence, and then transformed into an *E. coli* BL21 (DE3) host cell for expression.

A single bacterial colony is inoculated into a 50 ml LB liquid culture medium (containing 100 µg/ml ampicillin) and then subjected to shake culture for 14 h at 200 rpm and 37° C. The cultured product is transferred to a 200 ml TB culture medium (tryptone 1.2%, yeast powder 2.4%, glycerinum 0.4% (v/v), 17 mM $KH_2PO_4$, 72 mM $K_2HPO_4 \cdot 3H_2O$, and 100 µg/ml ampicillin) in an inoculation amount of 1% (V/V) and then subjected to shake culture at 37° C. until $OD_{600\ nm}$ is up to about 1.0, lactose is added to 1% (v/v), the above mixture is shaken at 25° C. with a speed of 200 rpm to induce expression for 15 h, and meanwhile a negative control is set (namely, lactose is not added for induction).

Fermentation broth is collected and centrifuged for 10 min at 10000 rpm to collect bacterial sludge, wet bacterial sludge is weighed, the bacterial sludge is resuspended with PBS in a ratio of 1:15 (g/ml), bacteria are broken three times with a homogenizer (AH100B, ATS Engineering Inc., Canada) at low temperature, and the pressure of the homogenizer is maintained to be 800~900 bar in the process of broking. After thallus is broken, broken cell solution is centrifuged (12000 rpm, 20 min) at 4° C., and supernatant is taken and subjected to 12% SDS-PAGE electrophoretic analysis. A result shows that there is an obvious expression band at the molecular weight of about 30 KD (shown in part A of FIG. 5), proving that the fusion protein is expressed in a soluble form.

Example 3 Cloning and Expression of a Long-Acting Fusion Protein EX-L21K-mhIgG1Fc of a High-Activity Exendin-4 Mutant With the coding gene (SEQ ID NO: 10) of the long-acting fusion protein EX-mhIgG1Fc of wild Exendin-4 in Example 2 as a template, it is mutated using an overlap extension site-directed mutagenesis method (Ho S N. *Gene*. 1989; 77:

51-9) to obtain the coding gene (SEQ ID NO: 12) of the long-acting fusion protein EX-L21K-mhIgG1Fc of the high-activity Exendin-4 mutant.

The following primers are synthesized by Nanjing Gen-Script Biotech Co., Ltd:

(1) forward mutation primer (EX-L21K-F):
(SEQ. ID NO: 17)
5'GGAAGAAGAAGCGGTTCGTAAATTCATCGAATGGCTGAAAAAC 3';

(2) reverse mutation primer (EX-L21K-R):
(SEQ ID NO: 18)
5'GTTTTTCAGCCATTCGATGAATTTACGAACCGCTTCTTCTTCC 3';

(3) external forward primer (NdeI-EX-F):
(SEQ ID NO: 19)
5'AGATATACATATGCACGGTGAAGGTACCTTCACCTCTGAC 3';

(4) external reverse primer (HindIII-Fc-R):
(SEQ ID NO: 20)
5'CGTCGACAAGCTTCTATTATTTACCCGGAGACAGAGACAGAG 3'.

Amplification of upstream fragment A: with the coding gene (SEQ ID NO: 10) of EX-mhIgG1Fc as a template, PCR is carried out under the action of Fastpfu DNA Polymerase (TransGen Biotech product). A 25 µl reaction system consists of an external forward primer (NdeI-EX-F) 10 pmol; a reverse mutation primer (EX-L21K-R) 10 pmol; Fast pfu DNA Polymerase 2.5 units; 5×reaction buffer 5 µl; dNTP (10 mM each) 0.5 µl; template plasmid DNA 0.5 µl (about 2.5 ng); and sterile water used for supplementation until the total volume is 25 µl. PCR conditions are as follows: denaturation is carried out for 2 minutes at 95° C.; cycle reaction of 30 cycles is then carried out: denaturation for 20 seconds at 95° C., annealing for 20 seconds at 50° C., and extension for 10 seconds at 72° C.; extension finally is carried out for 5 minutes at 72° C. After the reaction is ended, the product is identified with 1% agarose gel electrophoresis (AGE) and recovered with a TaKaRa gel recovery kit.

Amplification of downstream fragment B: with the coding gene (SEQ ID NO: 10) of EX-mhIgG1Fc as a template, and PCR is carried out under the action of Fastpfu DNA Polymerase (TransGen Biotech product). A 25 µl reaction system consists of a forward mutation primer (EX-L21K-F) 10 pmol; an external reverse primer (HindIII-Fc-R) 10 pmol; Fast pfu DNA Polymerase 2.5 units; 5×reaction buffer 5 µl; dNTP (10 mM each) 0.5 µl; template plasmid DNA 0.5 µl (about 2.5 ng); sterile water is used for supplementation until the volume is 25 µl. PCR conditions are as follows: denaturation is carried out for 2 minutes at 95° C.; cycle reaction of 30 cycles is then carried out: denaturation for 20 seconds at 95° C., annealing for 20 seconds at 50° C., and extension for 30 seconds at 72° C.; extension is finally carried out for 5 minutes at 72° C. The PCR product is identified with 1% agarose gel electrophoresis (AGE) and recovered with a TaKaRa gel recovery kit.

A complete mutant gene is obtained by overlap-extension PCR amplification: with a mixed solution of the upstream fragment A and the downstream fragment B as a template, PCR is carried out under the action of Taq plus DNA Polymerase (a product from TAKARA company). A 50 µl reaction system consists of an external forward primer (NdeI-EX-F) 10 pmol; an external reverse primer (HindIII-Fc-R) 10 pmol; Taq plus DNA Polymerase 2.5 units; 10×Taq plus buffer (with MgCl$_2$) 5 µl; dNTP (10 mM each) 1 µl; the mixed solution of the upstream fragment A and the downstream fragment B 1 µl (about 5 ng); sterile water is used for supplementation until the volume is 5 µl. PCR conditions are as follows: denaturation is carried out for 3 minutes at 95° C.; cycle reaction of 30 cycles is then carried out: denaturation for 30 seconds at 94° C., annealing for 30 seconds at 55° C., and extension for 1 minute at 72° C.; extension is finally carried out for 5 minutes at 72° C. The PCR product is identified with 1% agarose gel electrophoresis (AGE) and recovered with a TaKaRa gel recovery kit.

Figure 4:
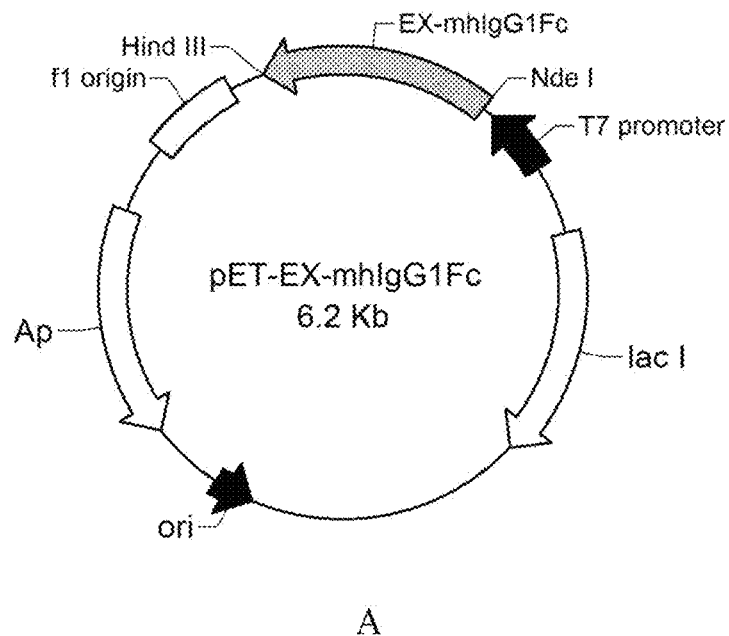
FIG. 4 is a structural diagram of a recombinant expression plasmid of the high-activity long-acting hypoglycemic fusion protein according to the disclosure. (A: a diagram of a recombinant plasmid pET-EX-mhIgG1Fc of the long-acting fusion protein EX-mhIgG1Fc of E. coli expressed wild Exendin-4, T7 promoter; AP: an ampicillin resistance gene; EX-mhIgG1Fc: a coding gene of the long-acting fusion protein EX-mhIgG1Fc of wild Exendin-4; Ori: a pET21b plasmid replication origin; and lac I: a lacI operon repressor protein. B: a diagram of a recombinant plasmid pET-EX-L21K-mh IgG1Fc of the long-acting fusion protein EX-L21K-mhIgG1Fc of E. coli expressed high-activity Exendin-4 (EX-L21K), T7 promoter; AP: an ampicillin resistance gene; EX-L21K-mhIgG1Fc: a coding gene of the long-acting fusion protein EX-L21K-mhIgG1Fc of high-activity Exendin-4 mutant (EX-L21K); Ori: a pET21b plasmid replication origin; and lac I: a lacI operon repressor protein. C. A diagram of a recombinant plasmid pET-EX-hIgG1Fc of the long-acting fusion protein EX-hIgG1Fc of E. coli expressed wild Exendin-4, T7 promoter; AP: an ampicillin resistance gene; EX-hIgG1Fc: a coding gene of the long-acting fusion protein EX-hIgG1Fc of wild Exendin-4; Ori: a pET21b plasmid replication origin; and lac I: a lacI operon repressor protein).
Figure 4:
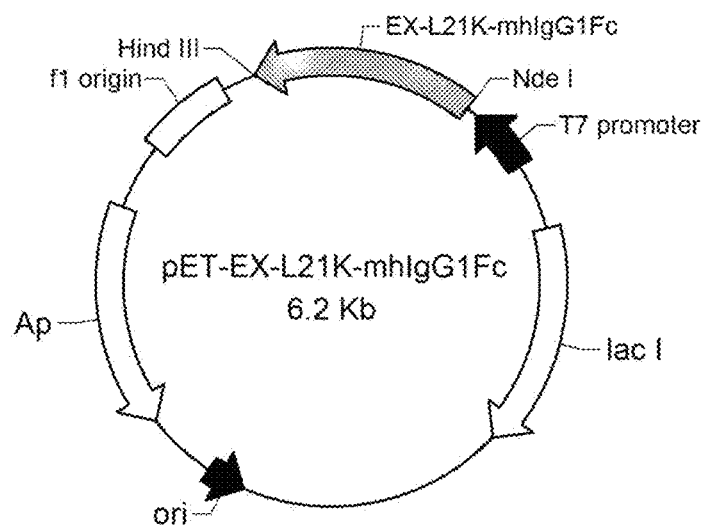

The obtained mutant gene is subjected to double-enzyme digestion with Nde I and Hind III and then cloned to a prokaryotic expression vector pET21b to construct an expression plasmid pET-EX-L21K-mhIgG1Fc (shown in part B of FIG. 4). A DNA sequence result shows that its gene sequence is identical to the gene sequence (SEQ ID NO: 12) of the long-acting fusion protein EX-L21K-mhIgG1Fc of the high-activity Exendin-4 mutant. The expression plasmid pET-EX-L21K-mhIgG1Fc is transformed into an *E. coli* BL21 (DE3) host, and the long-acting fusion protein EX-L21K-mhIgG1Fc of the high-activity Exendin-4 mutant is expressed with reference to the protein expression method in Example 2. After expression, broken cell solution is centrifuged at 4° C. (12000 rpm, 20 min), and supernatant is taken for 12% SDS-PAGE electrophoretic analysis. A result shows that there is an obvious protein expression hand at the molecular weight of about 30 KD (shown in part B of FIG. 5), proving that the fusion protein is expressed in a soluble form.

Example 4 Cloning and Expression of a Long-Acting Fusion Protein EX-hIgG1Fc of Wild Exendin-4

The coding gene (SEQ ID NO: 14) of a long-acting fusion protein EX-hIgG1Fc of wild Exendin-4 is synthesized and cloned by Nanjing Jinsirui Biotechnology Co., Ltd. The gene is subjected to double-enzyme digestion with Nde I and Hind III and then sub-cloned to a prokaryotic expression vector pET21b to construct an expression plasmid pET-EX-hIhG1Fc (FIG. 4C). After sequencing and verification, the expression plasmid is transformed into *E. coli* BL21 (DE3) host bacteria for expression using a CaCl$_2$ method.

The long-acting fusion protein EX-hIgG1Fc of Wild Exendin-4 is expressed with reference to the protein expression method in Example 2. After expression, broken cell solution is centrifuged at 4° C. (12000 rpm, 20 min), and supernatant is taken for 12% SDS-PAGE electrophoretic analysis. A result is that there is no target protein expression band at the molecular weight of about 30 KD, indicating that the fusion protein cannot be expressed in a soluble form.

Example 5 Separation and Purification of Fusion Proteins EX-mhIgG1Fc and EX-L21K-mhIgG1Fc 1. Collection of bacterial sludge and breaking of cell walls: fermentation broth is centrifuged at 42° C. (10000 rpm, 10 min) to collect bacterial sludge, wet bacterial sludge is weighed and resuspended with PBS buffer in a ratio of 1:15 (g/ml), and the bacterial sludge is washed twice to three times. The bacterial sludge is resuspended in a ratio of 10% (w/v) with broken bacterial buffer (PBS buffer (pH 7.4) containing 1 mM PMSF and 1 mM EDTA), cells are broken three times with an ATS homogenizer (AH100B, ATS Engineering Inc., Canada), and the pressure of the homogenizer in the process of broking is maintained to be 800~900 bar. The broken cells are centrifuged at 4° C. (12000 rpm, 20 min) to collect supernatant of broken wall solution.

2. Protein A affinity chromatography: a HiTrap rProtein A FF affinity chromatographic prepacked column (a product from GE company) is sufficiently balanced with balance buffer PBS (pH7.4). The supernatant of broken wall solution is subjected to suction filtration via a 0.22 μm water phase filter membrane, and then loaded at a flow velocity of 0.5 ml/min. After loading is completed, the chromatographic column is rinsed with the balance buffer to remove hybrid proteins that are not bound. Then, eluting is carried out with elution buffer (0.1M citric acid, pH is adjusted to 4.0 with NaOH), and 450 μl of neutralization buffer (which is formed by mixing 1M Tris hydrochloride buffer (pH is adjusted to 9.0) and glycerinum in a ratio of 1:2) is added into each ml of collected solution.

3. Ammonium sulfate precipitation: after filtered by the 0.22 μm membrane, ice-cold saturated ammonium sulfate solution is dropped into the above protein-like sample solution placed on ice bath at a flow velocity of 1 ml/min until a concentration is 60%, and a target protein is precipitated. Slow stirring is carried out with a magnetic stirrer in the whole process. Centrifugation is carried out at 4° C. (10000 rpm, 20 min) to collect precipitate, the collected precipitate is dissolved with a proper amount of PBS buffer (pH7.4) to obtain concentrated target protein solution.

4. Gel chromatography: a Superdex 200 Increase 10/300 GL gel filtration prepacked column (a product from GE Company) is sufficiently balanced with PBS buffer (pH7.4). 500 μl of concentrated target protein solution precipitated by ammonium sulfate is taken and centrifuged at 40° C. (10000 rpm, 10 min) to collect supernatant, the supernatant is loaded to the balanced chromatographic column at a flow velocity of 0.4 ml/min. Target protein eluting solution is collected and eluted, and filtered and sterilized with a 0.22 μm filter membrane on an ultra-clean platform. Subsequently, the obtained substance is sub-packed, and stored at −70° C.

Figure 5:
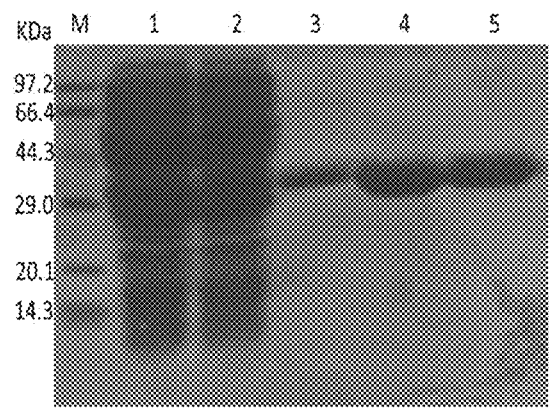
FIG. 5 shows an electrophoresis result of a high-activity long-acting hypoglycemic fusion protein according to the disclosure. (A: sample purity of long-acting fusion protein EX-mhIgG1Fc of wild Exendin-4 analyzed by 12% SDS-PAGE, wherein M: a low molecular weight protein marker; Lane 1: broken bacteria solution supernatant; Lane 2: protein A column penetrating solution; Lane 3: a sample purified by a protein A affinity column; Lane 4~5: samples purified by a Superdex molecular sieve. B: sample purity of a long-acting fusion protein EX-L21K-mhIgG1Fc of a high-activity Exendin-4 mutant (EX-L21K) analyzed by 12% SDS-PAGE, wherein M: a low molecular weight protein marker; Lane 1: broken bacteria solution supernatant; Lane 2~3: protein A column penetrating solution; Lane 4: a sample purified by a protein A affinity column; Lane 5: a sample purified by a Superdex molecular sieve).
Figure 5:
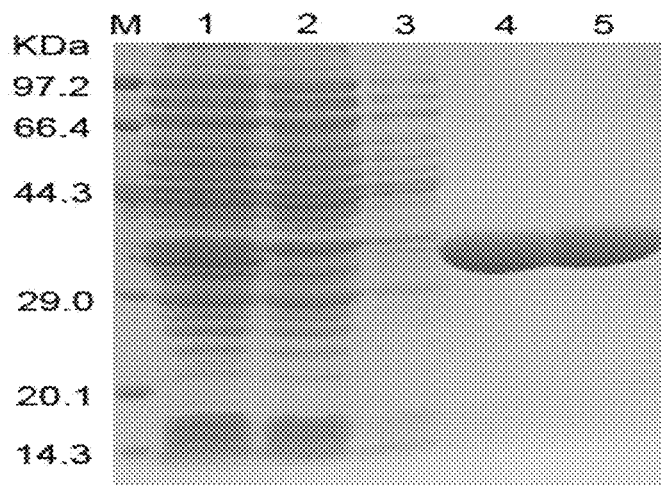

Samples collected in various steps are purified and subjected to 12% SDS-PAGE electrophoretic analysis. Results are seen in FIG. 5.

Example 6 Molecular Weight Detection and Purity Analysis of Fusion Proteins EX-mhIgG1Fc and EX-L21K-mhIgG1Fc Analysis is carried out on a high performance liquid chromatography (HPLC) system (LC-2010A HT, SHIMADZU Corp., Japan) utilizing Size Exclusion Chromatography (SEC), wherein, a chromatographic column is Shodex PROTEIN KW-802.5 (SHOW A DENKO K.K., Japan), a mobile phase is 0.2M phosphate buffer (pH7.4) and contains 0.1M $Na_2SO_4$ (which is added according to specification requirement of a chromatographic column), a flow velocity is 0.7 ml/min, and a detection wavelength is 280 nm.

Figure 6:
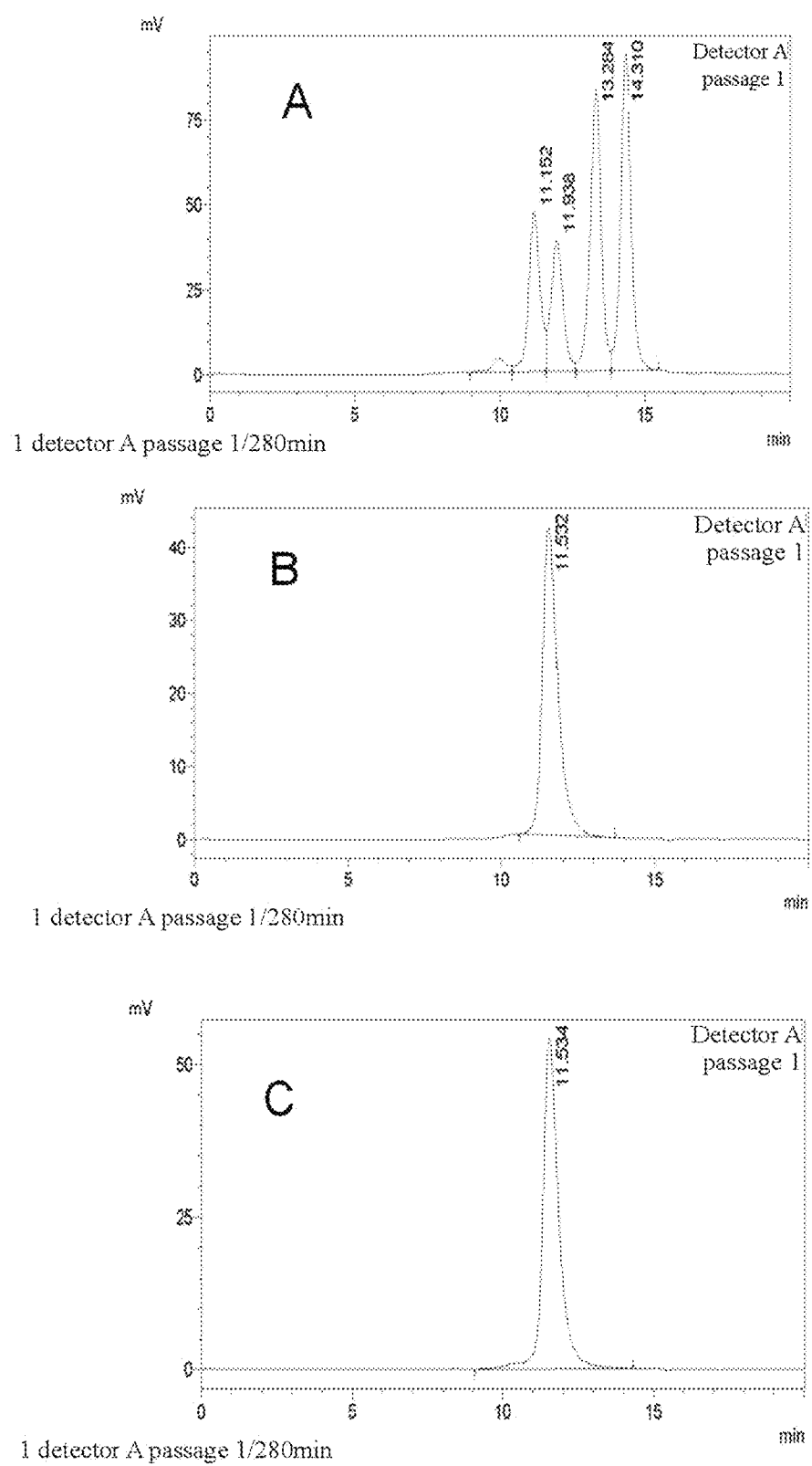
FIG. 6 shows molecular weight and purity results of a high-activity long-acting hypoglycemic fusion protein detected by SEC-HPLC chromatography according to the disclosure (chromatography column: Shodex PROTEIN KW-802.5, SHOWA DENKO K.K., Japan. A: analysis of four standard proteins: BSA (MW=67 kDa), chicken ovalbumin (MW=43 kDa), chymotrypsinogen (MW=25 kDa) and lysozyme (MW=14.4 kDa), their retention times are respectively 11.15 min, 11.94 min, 13.28 min and 14.31 min, corresponding retention volumes are respectively 7.81 ml, 8.36 ml, 9.30 ml and 10.02 ml. B: the long-acting fusion protein EX-mhIgG1Fc of purified Exendin-4 is analyzed, its retention time is 11.532 min, a corresponding retention volume is 8.07 ml, a computative molecular weight is 54.62 kDa, and the purity is up to 98.296%. C. The long-acting fusion protein EX-L21K-mhIgG1Fc of a purified Exendin-4 mutant (EX-L21K) is analyzed, its retention time is 11.534 min, a corresponding retention volume is 8.07 ml, an extrapolated molecular weight is 54.57 kDa, and the purity is up to 99.642%).

Single analysis and mixed analysis are carried out on four standard proteins purchased from Shanghai Yuanye Biotechnology Company. Results show that retention times of four standard proteins BSA (MW=67 kDa), chicken ovalbumin (MW=43 kDa), chymotrypsinogen (MW=25 kDa) and lysozyme (MW=14.4 kDa) are respectively 11.152 min, 11.938 min, 13.284 min and 14.31 min (shown in part A of FIG. 6), corresponding retention volumes are respectively 7.81 ml, 8.36 ml, 9.30 ml and 10.02 ml. Standard curves are made according to molecular weights and retention volumes of various standard proteins to obtain a molecular weight calculation formula:

$$1\ gMW = -0.2965 \times Ve + 4.1308.$$

The retention time of the long-acting fusion protein EX-mhIgG1Fc of wild Exendin-4 is 11.532 min, as shown in FIG. 6B, a corresponding retention volume is 8.07 ml, and a molecular weight calculated according to the above formula is 54.62 kDa and is close to the molecular weight 60.92 kDa of a dimer predicted in ExPASy website (web.expasy.org).

The retention time of the long-acting fusion protein EX-L21K-mhIgG1Fc of the high-activity Exendin-4 mutant is 11.534 min, as shown in FIG. 6C, a corresponding retention volume is 8.07 ml, and a molecular weight calculated according to the above formula is 54.57 kDa and is close to the molecular weight 60.98 kDa of a dimer predicted in ExPASy website (web.expasy.org). (http://web.expasy.org/compute_pi/).

Accordingly, the purified long-acting fusion protein EX-mhIgG1Fc of wild Exendin-4 and the long-acting fusion protein EX-L21K-mhIgG1Fc of the high-activity Exendin-4 mutant are both present in a soluble dimer form.

In addition, purity analysis is carried out on SEC-HPLC analysis results of the above two proteins by adopting a peak area comparison method. A result shows that the purity of the purified EX-mhIgG1Fc sample is 98.296% (shown in part B of FIG. 6), and the purity of the purified EX-L21K-mhIgG1Fc sample is 98.642% (shown in part C of FIG. 6).

Example 7 In-Vivo Hypoglycemic Test for Type II Diabetic Model Mouse C57BL/KsJ-db/db 50 six-week-old type II diabetic mice C57BL/KsJ-db/db (namely, S.Cg-Dock7$^m$+/+Lepr$^{db}$/JNju mouse) and 10 control mice C57BLKS/JNju are purchased from Nanjing Biomedical Research Institute of Nanjing University (certificate number: 201602819, and license number: SCXK (Su) 2015-0001). The mouse are fed in a SPF-grade animal house with a humidity of 40-60% at room temperature of 25° C. for 12 h each under light and dark conditions, and an experiment is carried out after adaptive feeding for one week. Blood glucose concentration is measured using a Roche Accu-Chek® Performa glucometer and blood glucose test paper. Experiment grouping and administration modes are seen in Table 1.

TABLE 1

Experimental Animal Grouping And Administrations

| Group | Mice | n | Drug | Administration dosage | Administration mode |
|---|---|---|---|---|---|
| 1 | C57BLKS/JNju | 8 | NS | — | ip. |
| 2 | BKS.Cg-Dock7$^m$+/+ Lepr$^{db}$/JNju | 8 | NS | — | ip. |
| 3 | BKS.Cg-Dock7$^m$+/+ Lepr$^{db}$/JNju | 8 | Ex-4 | 10 nmol/kg | ip. |
| 4 | BKS.Cg-Dock7$^m$+/+ Lepr$^{db}$/JNju | 8 | EX-mhIgG1Fc | 10 nmol/kg | ip. |
| 5 | BKS.Cg-Dock7$^m$+/+ Lepr$^{db}$/JNju | 8 | EX-L21K-mhIgG1Fc | 5 nmol/kg | ip. |
| 6 | BKS.Cg-Dock7$^m$+/+ Lepr$^{db}$/JNju | 8 | EX-L21K-mhIgG1Fc | 10 nmol/kg | ip. |
| 7 | BKS.Cg-Ddck7$^m$+/+ Lepr$^{db}$/JNju | 8 | EX-L21K-mhIgG1Fc | 20 nmol/kg | ip. |

Note:
NS is normal saline; Ex-4 is positive drag acetic Exendin-4, a product from Shanghai Gil Co., Ltd (CATALOG number: 052143; batch number: P160102-CQ052143; molecular formula: $C_{184}H_{282}N_{50}O_{60}S_1$; purity is 99.41%; molecular weight: 4186.66 Da).

1. Cute Hypoglycemic Test

Figure 7:
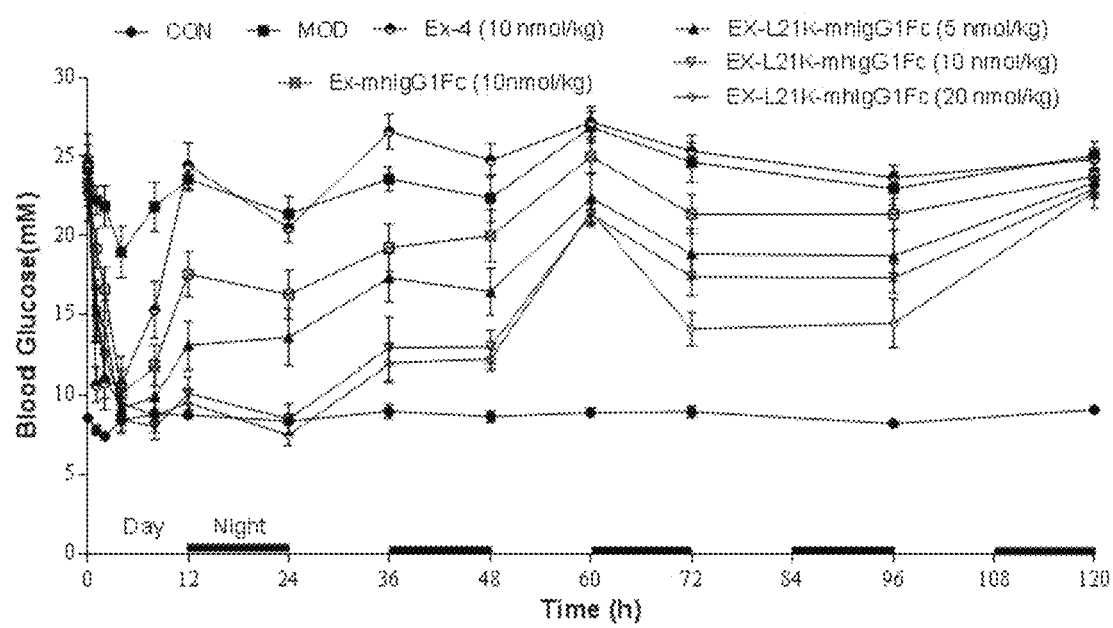
FIG. 7 shows influence of wild Exendin-4 (EX-4), a long-acting fusion protein (EX-mhIgG1Fc) of wild Exendin-4 and a long-acting fusion protein (EX-L21K-mhIgG1 Fc) of a high-activity Exendin-4 mutant on BKS.Cg-Dock7$^m$+/+Leqr$^{db}$/JNju mice blood glucose level after abdominal administration (n=8, means±SEM).

Blood glucose levels of each group of mouse are detected before administration. As shown in Table 2 and FIG. 7, blood glucose levels of a model group, Ex-4, EX-mhIgG1Fc and EX-L21K-mhIgG1Fc (5-20 nmol/kg) are respectively 24±0.81, 24.53±1.20, 23.31±1.05, 23.04±1.23, 22.41±1.51 and 24.99±1.43 mM. There is a significant difference (P<0.0001) compared with 8.58±0.25 mM in a normal control group. There is no difference between the model group and various drug groups, indicating that BKS.Cg-Dock7$^m$+/+Lepr$^{db}$/JNju has become diabetics. Moreover, there is no difference between the drug groups and the model group, and subsequent experiments can be carried out.

After mouse are administrated, blood glucose levels after administration for 1, 2, 4, 8, 12, 24, 36, 48, 60, 72, 96 and 120 h are continuously monitored. Results are as shown in Table 2 and FIG. 7. After administration for 1 h, Ex-4 and EX-L21K-mhIgG1Fc (5-20 nmol/kg) groups have obvious hypoglycemic effects, and the EX-mhIgG1Fc group exhibits its hypoglycemic effect until 2 h (P<0.01 vs model group), and various drug groups still exhibit strong hypoglycemic activities after administration for 8 h (P<0.0001 vs model group). The blood glucoses of mouse in Ex-4 group are gradually raised back to a level before administration, and the blood glucoses of mouse in EX-mhIgG1Fc group are gradually raised back to a level before administration after administration for 48 h. The hypoglycemic effects of various dosage group of EX-L21K-mhIgG1Fc are more durable, wherein, the hypoglycemic effect of 5 nmol/kg EX-L21K-mhIgG1Fc lasts until 72 h after administration (P<0.01 vs model group), the hypoglycemic effects of 10 nmol/kg EX-L21K-mhIgG1Fc (P<0.01 vs model group) and 20 nmol/kg EX-L21K-mhIgG1Fc (P<0.0001 vs model group) are still present after administration for 96 h.

Figure 8:
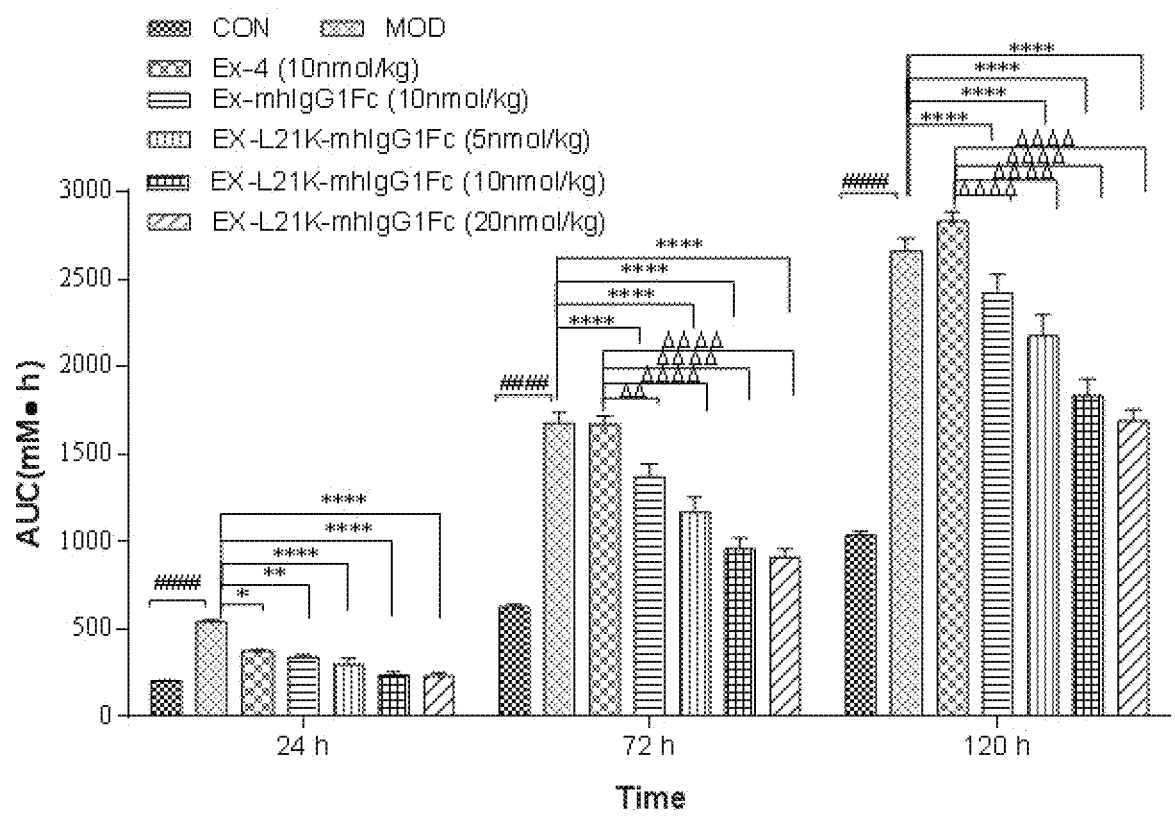
FIG. 8 shows influence of wild Exendin-4 (EX-4), a long-acting fusion protein (EX-mhIgG1Fc) of wild Exendin-4 and a long-acting fusion protein (EX-L21K-mhIgG1Fc) of a high-activity Exendin-4 mutant on BKS.Cg-Dock7$^m$+/+Leqr$^{db}$/JNju mice blood glucose level after abdominal administration. $AUC_{0\text{-}120\ h}$ is as shown in FIG. 8. #### represents $p<0.0001$ as compared with normal group; *,  and * respectively represent $p<0.05$, $p<0.01$ and $p<0.0001$ as compared with model group; ΔΔ and ΔΔΔ respectively represent $p<0.01$ and $p<0.0001$ as compared with Ex-4 group (n=8, means±SEM).

Hypoglycemic effects of Ex-4, EX-mhIgG1Fc and EX-L21K-mhIgG1Fc (5-20 nmol/kg) are further analyzed and estimated using a method of area under the curve (AUC). As shown in FIG. 8, compared with normal control group, $AUC_{0-24\,h}$, $AUC_{0-72\,h}$ and $AUC_{0-120\,h}$ in model group are significantly increased (p<0.0001). After Ex-4, EX-mhIgG1Fc and EX-L21K-mhIgG1Fc (5-20 nmol/kg) are administrated, $AUCs_{0-24\,h}$ are respectively reduced to 374.46±6.20 mM·h (p<0.005 vs model group), 337.76±13.35 mM·h (p<0.0001 vs model group), 296.69±34.39 mM·h (p<0.0001 vs model group), 237.34±16.87 mM·h (p<0.0001 vs model group), and 230.80±20.09 mM·h (p<0.0001 vs model group). Compared with Ex-4, $AUCs_{0-24\,h}$ of various groups of EX-mhIgG1Fc and EX-L21K-mhIgG1Fc (5-20 nmol/kg) drugs has no significant difference. $AUCs_{0-72\,h}$ and $AUCs_{0-120\,h}$ of various groups of EX-mhIgG1Fc and EX-L21K-mhIgG1Fc (5-20 nmol/kg) are all significantly reduced compared with those of model group, and there is no significant change between Ex-4 group and model group.

In summary, three drugs Ex-4, EX-mhIgG1Fc and EX-L21K-mhIgG1Fc (5-20 nmol/kg) all have hypoglycemic effects, among them, Ex-4 fast works and exhibits a significant hypoglycemic effect after administration for 1 h. EX-mhIgG1Fc relatively slowly works and exhibits the hypoglycemic effect of after administration for 2 h, but its hypoglycemic effect lasts for a long time and can be extended to 48 h after administration. EX-L21K-mhIgG1Fc exhibits the hypoglycemic effect within 1 h after administration, and its hypoglycemic effect lasts for a longer time and can be extended to 96 h after administration.

TABLE 2

Hypoglycemic Activity of Ex-4/FC and EX-L21K on BKS.Cg-Dock7$^m$ +/+ Lepr$^{db}$/JNju Mouse

| Administration time (h) | Blood glucose (mM) | | | | | | |
|---|---|---|---|---|---|---|---|
| | CON | MOD | Ex-4 (10 nmol/kg) | EX-mhIgG1Fc (10 nmol/kg) | EX-L21K-mhIgG1Fc (5 nmol/kg) | EX-L21K-mhIgG1Fc (10 nmol/kg) | EX-L21K-mhIgG1Fc (20 nmol/kg) |
| 0 | 8.58 ± 0.25 | 24.16 ± 0.81#### | 24.53 ± 1.20#### | 23.31 1.05#### | 23.04 ± 1.23#### | 22.41 ± 1.51#### | 24.99 ± 1.43#### |
| 1 | 7.79 ± 0.33 | 22.23 ± 0.90 | 10.63 ± 1.07** | 19.18 ± 1.27ΔΔΔΔ | 15.18 ± 1.58*Δ | 15.2 ± 1.98*Δ | 14.98 ± 1.65*Δ |
| 2 | 7.40 ± 0.21 | 21.88 ± 1.28 | 10.79 ± 1.70* | 16.6 ± 1.40ΔΔ | 11.28 ± 1.49** | 14.3 ± 1.58 | 12.46 ± 1.36** |
| 4 | 8.45 ± 0.30 | 18.96 ± 1.64 | 10.71 ± 1.65**** | 10.08 ± 1.49**** | 9.16 ± 1.42**** | 8.48 ± 0.89**** | 9.54 ± 1.20**** |
| 8 | 8.79 ± 0.34 | 21.81 ± 1.55 | 15.31 ± 1.79** | 11.83 ± 1.24 | 9.91 ± 1.84ΔΔ | 8.01 ± 0.78ΔΔΔΔ | 8.73 ± 1.08**ΔΔΔ |
| 12 | 8.76 ± 0.23 | 23.58 ± 0.74 | 24.43 ± 1.44 | 17.58 ± 1.41ΔΔΔ | 13.06 ± 1.51ΔΔΔΔ | 10.13 ± 1.03ΔΔΔΔ | 53 ± 0.75**ΔΔΔΔ |
| 24 | 8.38 ± 0.17 | 21.36 ± 1.10 | 20.48 ± 0.88 | 16.28 ± 1.53* | 13.58 ± 1.80**ΔΔΔ | 8.5 ± 0.96ΔΔΔΔ | 7.49 ± 0.66**ΔΔΔΔ |
| 36 | 8.99 ± 0.43 | 23.59 ± 0.75 | 26.59 ± 1.11 | 19.24 ± 1.49*ΔΔΔΔ | 17.34 ± 1.53ΔΔΔΔ | 12.9 ± 1.96ΔΔΔΔ | 11.95 ± 1.16**ΔΔΔΔ |
| 48 | 8.65 ± 0.37 | 22.38 ± 1.48 | 24.76 ± 1.06 | 19.99 ± 1.64Δ | 16.46 ± 1.48ΔΔΔΔ | 12.96 ± 1.06ΔΔΔΔ | 12.2 ± 0.63**ΔΔΔΔ |
| 60 | 8.91 ± 0.29 | 26.86 ± 0.99 | 27.19 ± 0.95 | 25.01 ± 1.06 | 22.39 ± 1.52*Δ | 21.36 ± 0.64ΔΔ | 21.5 ± 0.90ΔΔ |
| 72 | 8.95 ± 0.38 | 24.64 ± 1.26 | 25.34 ± 1.01 | 21.36 ± 1.23 | 18.85 ± 1.59ΔΔΔ | 17.4 ± 1.21*ΔΔΔΔ | 14.1 ± 1.06****ΔΔΔΔ |
| 96 | 8.21 ± 0.24 | 22.98 ± 1.06 | 23.68 ± 0.75 | 21.35 ± 0.98 | 18.71 ± 1.59Δ | 17.33 ± 0.95ΔΔΔ | 14.46 ± 1.54**ΔΔΔΔ |
| 120 | 9.08 ± 0.27 | 25.08 ± 0.85 | 24.83 ± 0.68 | 23.75 ± 1.12 | 23.35 ± 0.87 | 22.96 ± 0.65 | 22.76 ± 1.03 |

Note:
compared with normal group, #### represents P < 0.0001;
compared with model group, *, , * and **** respectively represents P < 0.05, P > 0.01, P < 0.001 and P < 0.0001;
compared with Ex-4, Δ, ΔΔ, ΔΔΔ and ΔΔΔΔ respectively represents P < 0.05, P < 0.01, P < 0.001 and P < 0.0001;
(n = 8, means ± SEM).

2. Intraperitoneal Glucose Tolerance Test (IPGTT)

Various groups of animals are fasted overnight for 18 h before test. Firstly, normal saline, Ex-4, EX-mhIgG1Fc and EX-L21K-mhIgG1Fc are respectively intraperitoneally injected. After administration for 2 h, 1.5 g/kg glucose is intraperitoneally injected to each mouse, blood is taken via caudal vein, and blood glucose concentrations in −120, 0, 15, 30, 45, 60, 90, 120 and 180 min are recorded. During the test, animals are normally dieted and supplied with water.

Figure 9:
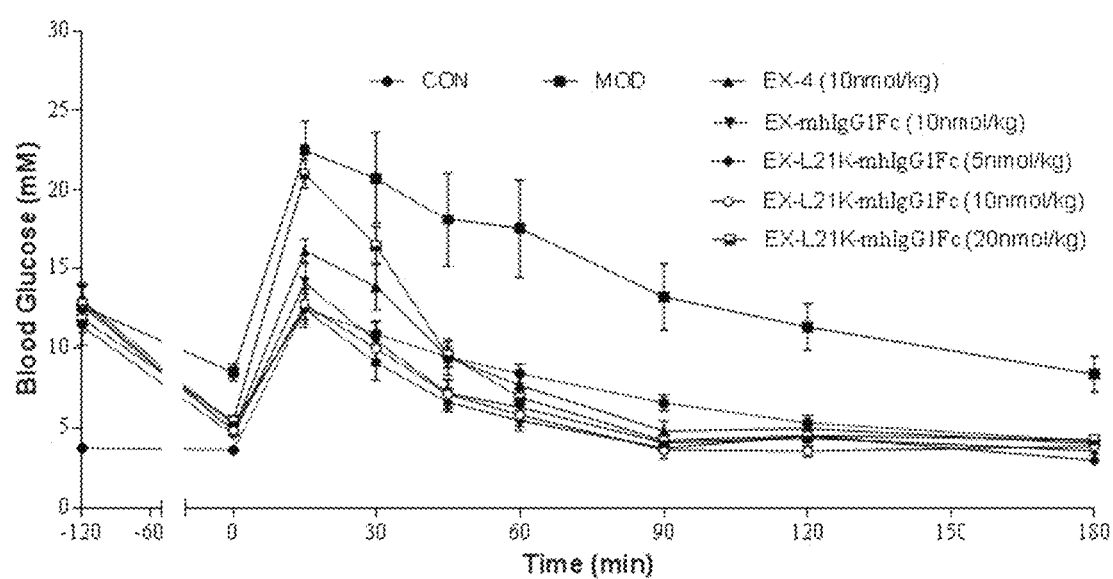
FIG. 9 shows influence of wild Exendin-4 (EX-4), a long-acting fusion protein (EX-mhIgG1Fc) of wild Exendin-4 and a long-acting fusion protein (EX-L21K-mhIgG1Fc) of a high-activity Exendin-4 mutant on BKS.Cg-Dock7$^m$+/+Leqr$^{db}$/JNju mice IPGTT (n=8, means±SEM).

IPGTT test results are seen in FIG. 9. After 10 nmol/kg Ex-4, 10 nmol/kg EX-mhIgG1Fc and 5-20 nmol/kg EX-L21K-mhIgG1Fc are administered, the fasting blood glucoses of mouse are all significantly reduced ($P<0.0001$ vs model group). After 1.5 g/kg glucose is intraperitoneally injected for 15 min, the blood glucoses of mouse in model group are raised from $8.49\pm0.54$ to $22.55\pm1.77$ mM and always maintained at a high level, and after being intraperitoneally injected with glucose, although the blood glucoses of mouse in various Ex-4, EX-mhIgG1Fc and EX-L21K-mhIgG1Fc drug groups are raised, they are fast reduced to a normal level and continuously maintained at a low level, and are not raised to a level before the glucose is given until 180 min after administration.

Figure 10:
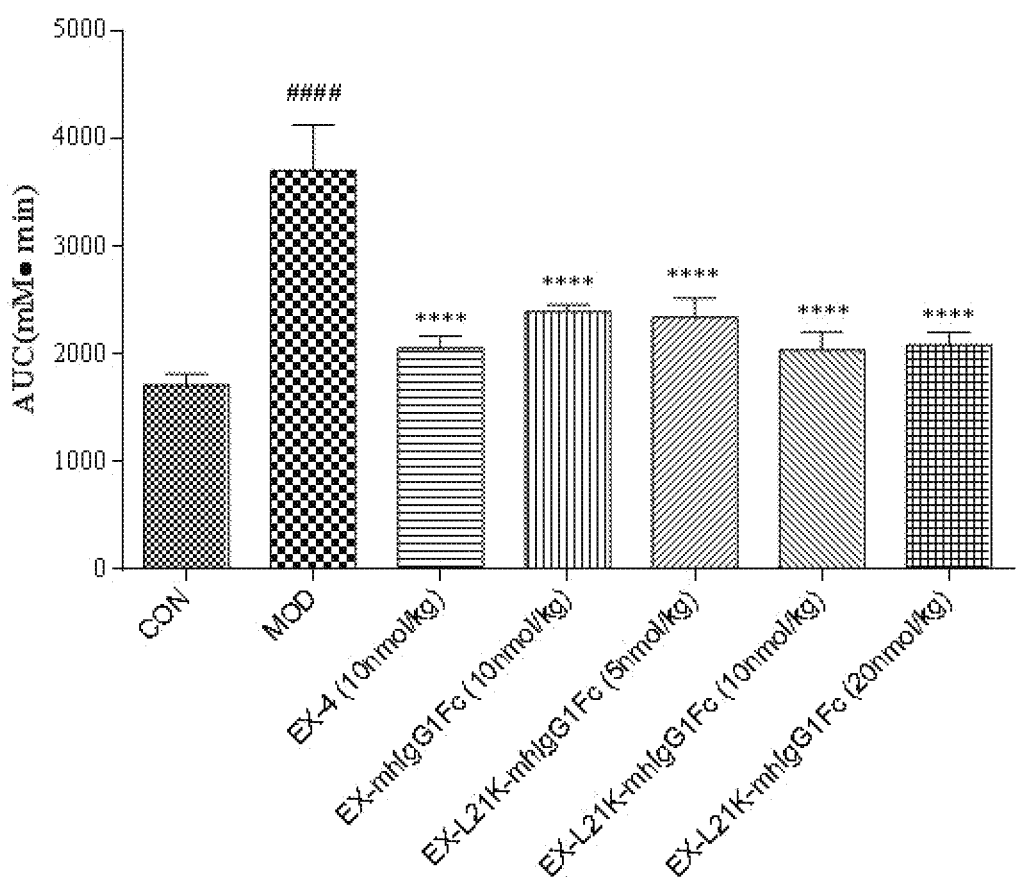
FIG. 10 shows influence of wild Exendin-4 (EX-4), a long-acting fusion protein (EX-mhIgG1Fc) of wild Exendin-4 and a long-acting fusion protein (EX-L21K-mhIgG1Fc) of a high-activity Exendin-4 mutant on glucose tolerance of diabetic mouse.

Area under the curve is further applied for analysis. Results are as shown in FIG. 10, compared with normal control group, $AUCs_{0-180\ min}$ in model group are significantly increased ($p<0.0001$). Firstly, 10 nmol/kg Ex-4, 10 nmol/kg EX-mhIgG1Fc and 5-20 nmol/kg EX-L21K-mhIgG1Fc are administered to pre-act for 120 min, 1.5 g/kg glucose is then intraperitoneally injected, $AUCs_{0-180\ min}$ are respectively reduced to $2058\pm109.5$ ($p<0.0001$ vs model group), $2397\pm62.49$ ($p<0.0001$ vs model group), $2338\pm181.2$ ($p<0.0001$ vs model group), $2035\pm169.6$ ($p<0.0001$ vs model group) and $2082\pm119.9$ mM·min ($p<0.0001$ vs model group). Accordingly, all of Ex-4, EX-mhIgG1Fc and EX-L21K-mhIgG1Fc can significantly enhance the tolerance of diabetic mouse on glucose.

We claim:

1. A high-activity long-acting hypoglycemic fusion protein, wherein the hypoglycemic fusion protein is formed by connecting, via a linker peptide or directly, a high-activity Exendin-4 mutant with a mutated Fc fragment of a human immunoglobulin IgG1; the amino acid sequence of the fusion protein is as shown in SEQ ID NO: 11, SEQ ID NO: 15 or SEQ ID NO: 16.

2. The hypoglycemic fusion protein according to claim 1, wherein, the mutated Fc fragment of the human immunoglobulin IgG1 comprises an mutated human IgG1 hinge region and human IgG1 constant regions CH2 and CH3, and the amino acid sequence of the mutated human IgG1 hinge region is as shown in SEQ ID NO: 6.

3. The hypoglycemic fusion protein according to claim 2, wherein, the amino acid sequences of the human IgG1 constant regions CH2 and CH3 are as shown in SEQ ID NO: 7.

4. The hypoglycemic fusion protein according to claim 1, wherein, the linker peptide is a flexible peptide rich in Gly and/or Ala and/or Ser, having 1~50 amino acid residues in length.

5. The hypoglycemic fusion protein according to claim 4, wherein, the amino acid sequence of the linker peptide is as shown in SEQ ID NO: 8.

6. The hypoglycemic fusion protein according to claim 1, wherein, the amino acid sequence of the high-activity Exendin-4 mutant is as shown in SEQ ID NO:2, SEQ ID NO: 3, or SEQ ID NO: 4.

7. A method of making a composition comprising the hypoglycemic fusion protein of claim 1.

* * * * *

```
                          SEQUENCE LISTING

<160> NUMBER OF SEQ ID NOS: 20

<210> SEQ ID NO 1
<211> LENGTH: 39
<212> TYPE: PRT
<213> ORGANISM: Artificial Sequence
<220> FEATURE:
<223> OTHER INFORMATION: Synthesized

<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 2
<211> LENGTH: 39
<212> TYPE: PRT
<213> ORGANISM: Artificial Sequence
<220> FEATURE:
<223> OTHER INFORMATION: Synthesized

<400> SEQUENCE: 2

His Gly Glu Gly Thr Phe Thr Ser Asp Leu Ser Lys Gln Met Glu Glu
1               5                   10                  15

Glu Ala Val Arg Lys Phe Ile Glu Trp Leu Lys Asn Gly Gly Pro Ser
            20                  25                  30

Ser Gly Ala Pro Pro Pro Ser
        35

<210> SEQ ID NO 3
<211> LENGTH: 39
<212> TYPE: PRT
<213> ORGANISM: Artificial Sequence
<220> FEATURE:
<223> OTHER INFORMATION: Synthesized

<400> SEQUENCE: 3

His Gly Glu Gly Thr Phe Thr Ser Asp Leu Ser Lys Gln Met Glu Glu
1               5                   10                  15

Glu Ala Val Arg Arg Phe Ile Glu Trp Leu Lys Asn Gly Gly Pro Ser
            20                  25                  30
```

Ser Gly Ala Pro Pro Pro Ser
        35

<210> SEQ ID NO 4
<211> LENGTH: 39
<212> TYPE: PRT
<213> ORGANISM: Artificial Sequence
<220> FEATURE:
<223> OTHER INFORMATION: Synthesized

<400> SEQUENCE: 4

His Gly Glu Gly Thr Phe Thr Ser Asp Leu Ser Lys Gln Met Glu Glu
1               5                   10                  15

Glu Ala Val Arg His Phe Ile Glu Trp Leu Lys Asn Gly Gly Pro Ser
            20                  25                  30

Ser Gly Ala Pro Pro Pro Ser
        35

<210> SEQ ID NO 5
<211> LENGTH: 16
<212> TYPE: PRT
<213> ORGANISM: Artificial Sequence
<220> FEATURE:
<223> OTHER INFORMATION: Synthesized

<400> SEQUENCE: 5

Val Glu Pro Lys Ser Cys Asp Lys Thr His Thr Cys Pro Pro Cys Pro
1               5                   10                  15

<210> SEQ ID NO 6
<211> LENGTH: 16
<212> TYPE: PRT
<213> ORGANISM: Artificial Sequence
<220> FEATURE:
<223> OTHER INFORMATION: Synthesized

<400> SEQUENCE: 6

Ser Gly Gly Gly Gly Ser Asp Lys Thr His Thr Cys Pro Pro Cys Pro
1               5                   10                  15

<210> SEQ ID NO 7
<211> LENGTH: 217
<212> TYPE: PRT
<213> ORGANISM: Artificial Sequence
<220> FEATURE:
<223> OTHER INFORMATION: Synthesized

<400> SEQUENCE: 7

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

```
Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215
```

<210> SEQ ID NO 8
<211> LENGTH: 4
<212> TYPE: PRT
<213> ORGANISM: Artificial Sequence
<220> FEATURE:
<223> OTHER INFORMATION: Synthesized

<400> SEQUENCE: 8

```
Gly Gly Gly Gly
1
```

<210> SEQ ID NO 9
<211> LENGTH: 277
<212> TYPE: PRT
<213> ORGANISM: Artificial Sequence
<220> FEATURE:
<223> OTHER INFORMATION: Synthesized

<400> SEQUENCE: 9

```
Met His Gly Glu Gly Thr Phe Thr Ser Asp Leu Ser Lys Gln Met Glu
1               5                   10                  15

Glu Glu Ala Val Arg Leu Phe Ile Glu Trp Leu Lys Asn Gly Gly Pro
            20                  25                  30

Ser Ser Gly Ala Pro Pro Pro Ser Gly Gly Gly Ser Gly Gly Gly
        35                  40                  45

Gly Ser Asp Lys Thr His Thr Cys Pro Pro Cys Pro Ala Pro Glu Leu
    50                  55                  60

Leu Gly Gly Pro Ser Val Phe Leu Phe Pro Pro Lys Pro Lys Asp Thr
65                  70                  75                  80

Leu Met Ile Ser Arg Thr Pro Glu Val Thr Cys Val Val Val Asp Val
                85                  90                  95

Ser His Glu Asp Pro Glu Val Lys Phe Asn Trp Tyr Val Asp Gly Val
            100                 105                 110

Glu Val His Asn Ala Lys Thr Lys Pro Arg Glu Glu Gln Tyr Asn Ser
        115                 120                 125

Thr Tyr Arg Val Val Ser Val Leu Thr Val Leu His Gln Asp Trp Leu
    130                 135                 140

Asn Gly Lys Glu Tyr Lys Cys Lys Val Ser Asn Lys Ala Leu Pro Ala
145                 150                 155                 160

Pro Ile Glu Lys Thr Ile Ser Lys Ala Lys Gly Gln Pro Arg Glu Pro
                165                 170                 175

Gln Val Tyr Thr Leu Pro Pro Ser Arg Asp Glu Leu Thr Lys Asn Gln
```

```
                180                 185                 190
Val Ser Leu Thr Cys Leu Val Lys Gly Phe Tyr Pro Ser Asp Ile Ala
            195                 200                 205

Val Glu Trp Glu Ser Asn Gly Gln Pro Glu Asn Asn Tyr Lys Thr Thr
        210                 215                 220

Pro Pro Val Leu Asp Ser Asp Gly Ser Phe Phe Leu Tyr Ser Lys Leu
225                 230                 235                 240

Thr Val Asp Lys Ser Arg Trp Gln Gln Gly Asn Val Phe Ser Cys Ser
                245                 250                 255

Val Met His Glu Ala Leu His Asn His Tyr Thr Gln Lys Ser Leu Ser
            260                 265                 270

Leu Ser Pro Gly Lys
            275

<210> SEQ ID NO 10
<211> LENGTH: 846
<212> TYPE: PRT
<213> ORGANISM: Artificial Sequence
<220> FEATURE:
<223> OTHER INFORMATION: Synthesized

<400> SEQUENCE: 10

Cys Ala Thr Ala Thr Gly Cys Ala Cys Gly Gly Thr Gly Ala Ala Gly
1               5                   10                  15

Gly Thr Ala Cys Cys Thr Thr Cys Ala Cys Cys Thr Cys Thr Gly Ala
            20                  25                  30

Cys Cys Thr Gly Thr Cys Thr Ala Ala Cys Ala Gly Ala Thr Gly Gly
        35                  40                  45

Gly Ala Ala Gly Ala Ala Gly Ala Ala Gly Cys Gly Gly Thr Thr Cys
    50                  55                  60

Gly Thr Cys Thr Gly Thr Thr Cys Ala Thr Cys Gly Ala Ala Thr Gly
65              70                  75                  80

Gly Cys Thr Gly Ala Ala Ala Ala Cys Gly Gly Thr Gly Gly Thr Thr
            85                  90                  95

Cys Cys Gly Thr Cys Thr Thr Cys Thr Gly Gly Thr Cys Gly Gly Cys
        100                 105                 110

Cys Gly Cys Cys Gly Cys Cys Gly Thr Cys Thr Gly Gly Thr Gly Gly
    115                 120                 125

Thr Gly Gly Thr Gly Gly Thr Thr Cys Thr Gly Gly Thr Gly Gly Thr
        130                 135                 140

Gly Gly Thr Gly Gly Thr Thr Cys Thr Gly Ala Cys Ala Ala Ala Ala
145                 150                 155                 160

Cys Cys Cys Ala Cys Ala Cys Thr Gly Cys Cys Cys Gly Cys Cys
        165                 170                 175

Gly Thr Gly Cys Cys Cys Gly Cys Gly Cys Cys Gly Gly Ala Ala
    180                 185                 190

Cys Thr Gly Cys Thr Gly Gly Thr Gly Gly Thr Cys Cys Gly Thr
        195                 200                 205

Cys Thr Gly Thr Thr Thr Cys Cys Thr Gly Thr Thr Cys Cys Cys
    210                 215                 220

Gly Cys Cys Gly Ala Ala Ala Cys Cys Gly Ala Ala Gly Ala Cys
225                 230                 235                 240

Ala Cys Cys Cys Thr Gly Ala Thr Gly Ala Thr Cys Thr Cys Thr
            245                 250                 255

Gly Thr Ala Cys Cys Cys Gly Gly Ala Ala Gly Thr Thr Ala Cys
```

-continued

```
            260                 265                 270
Cys Thr Gly Cys Gly Thr Thr Gly Thr Thr Gly Thr Thr Gly Ala Cys
        275                 280                 285

Gly Thr Thr Thr Cys Thr Cys Ala Cys Gly Ala Ala Gly Ala Cys Cys
    290                 295                 300

Cys Gly Gly Ala Ala Gly Thr Thr Ala Ala Ala Thr Thr Cys Ala Ala
305                 310                 315                 320
Cys Thr Gly Gly Thr Ala Cys Gly Thr Thr Gly Ala Cys Gly Gly Thr
                325                 330                 335

Gly Thr Thr Gly Ala Ala Gly Thr Thr Cys Ala Cys Ala Ala Cys Gly
            340                 345                 350
Cys Gly Ala Ala Ala Ala Cys Cys Ala Ala Ala Cys Cys Gly Cys Gly
        355                 360                 365

Thr Gly Ala Ala Gly Ala Ala Cys Ala Gly Thr Ala Cys Ala Ala Cys
    370                 375                 380

Thr Cys Thr Ala Cys Cys Thr Ala Cys Cys Gly Thr Gly Thr Thr Gly
385                 390                 395                 400
Thr Thr Thr Cys Thr Gly Thr Thr Cys Thr Gly Ala Cys Cys Gly Thr
                405                 410                 415

Thr Cys Thr Gly Cys Ala Cys Cys Ala Gly Gly Ala Cys Thr Gly Gly
            420                 425                 430

Cys Thr Gly Ala Ala Cys Gly Gly Thr Ala Ala Ala Gly Ala Ala Thr
        435                 440                 445

Ala Cys Ala Ala Ala Thr Gly Cys Ala Ala Ala Gly Thr Thr Thr Cys
    450                 455                 460

Thr Ala Ala Cys Ala Ala Ala Gly Cys Gly Cys Thr Gly Cys Cys Gly
465                 470                 475                 480

Gly Cys Gly Cys Cys Gly Ala Thr Cys Gly Ala Ala Ala Ala Ala Ala
                485                 490                 495

Cys Cys Ala Thr Cys Thr Cys Thr Ala Ala Ala Gly Cys Gly Ala Ala
            500                 505                 510

Ala Gly Gly Thr Cys Ala Gly Cys Cys Gly Cys Gly Thr Gly Ala Ala
        515                 520                 525

Cys Cys Gly Cys Ala Gly Gly Thr Thr Thr Ala Cys Ala Cys Cys Cys
    530                 535                 540

Thr Gly Cys Cys Gly Cys Cys Gly Thr Cys Thr Cys Gly Thr Gly Ala
545                 550                 555                 560

Cys Gly Ala Ala Cys Thr Gly Ala Cys Cys Ala Ala Ala Ala Ala Cys
                565                 570                 575

Cys Ala Gly Gly Thr Thr Thr Cys Thr Cys Thr Gly Ala Cys Cys Thr
            580                 585                 590

Gly Cys Cys Thr Gly Gly Thr Thr Ala Ala Ala Gly Gly Thr Thr Thr
        595                 600                 605

Cys Thr Ala Cys Cys Cys Gly Thr Cys Thr Gly Ala Cys Ala Thr Cys
    610                 615                 620

Gly Cys Gly Gly Thr Thr Gly Ala Ala Thr Gly Gly Gly Ala Ala Thr
625                 630                 635                 640

Cys Thr Ala Ala Cys Gly Gly Thr Cys Ala Gly Cys Cys Gly Gly Ala
                645                 650                 655

Ala Ala Ala Cys Ala Ala Cys Thr Ala Cys Ala Ala Ala Ala Cys Cys
            660                 665                 670

Ala Cys Cys Cys Cys Gly Cys Cys Gly Gly Thr Thr Cys Thr Gly Gly
        675                 680                 685
```

```
Ala Cys Thr Cys Thr Gly Ala Cys Gly Gly Thr Thr Cys Thr Thr Thr
    690                 695                 700
Cys Thr Thr Cys Cys Thr Gly Thr Ala Cys Thr Cys Thr Ala Ala Ala
705                 710                 715                 720
Cys Thr Gly Ala Cys Cys Gly Thr Thr Gly Ala Cys Ala Ala Ala Thr
                725                 730                 735
Cys Thr Cys Gly Thr Gly Gly Cys Ala Gly Cys Ala Gly Gly Gly
        740                 745                 750
Thr Ala Ala Cys Gly Thr Thr Thr Thr Cys Thr Cys Thr Thr Gly Cys
            755                 760                 765
Thr Cys Thr Gly Thr Thr Ala Thr Gly Cys Ala Cys Gly Ala Ala Gly
    770                 775                 780
Cys Gly Cys Thr Gly Cys Ala Cys Ala Ala Cys Cys Ala Cys Thr Ala
785                 790                 795                 800
Cys Ala Cys Cys Ala Gly Ala Ala Ala Thr Cys Thr Cys Thr Gly Thr
                805                 810                 815
Thr Cys Thr Cys Thr Gly Thr Cys Thr Cys Cys Gly Gly Thr Ala
        820                 825                 830
Ala Ala Thr Ala Ala Thr Ala Gly Ala Ala Gly Cys Thr Thr
        835                 840                 845
```

<210> SEQ ID NO 11
<211> LENGTH: 277
<212> TYPE: PRT
<213> ORGANISM: Artificial Sequence
<220> FEATURE:
<223> OTHER INFORMATION: Synthesized

<400> SEQUENCE: 11

```
Met His Gly Glu Gly Thr Phe Thr Ser Asp Leu Ser Lys Gln Met Glu
1               5                   10                  15
Glu Glu Ala Val Arg Lys Phe Ile Glu Trp Leu Lys Asn Gly Gly Pro
            20                  25                  30
Ser Ser Gly Ala Pro Pro Pro Ser Gly Gly Gly Ser Gly Gly Gly
        35                  40                  45
Gly Ser Asp Lys Thr His Thr Cys Pro Pro Cys Pro Ala Pro Glu Leu
    50                  55                  60
Leu Gly Gly Pro Ser Val Phe Leu Phe Pro Pro Lys Pro Lys Asp Thr
65                  70                  75                  80
Leu Met Ile Ser Arg Thr Pro Glu Val Thr Cys Val Val Val Asp Val
                85                  90                  95
Ser His Glu Asp Pro Glu Val Lys Phe Asn Trp Tyr Val Asp Gly Val
            100                 105                 110
Glu Val His Asn Ala Lys Thr Lys Pro Arg Glu Glu Gln Tyr Asn Ser
        115                 120                 125
Thr Tyr Arg Val Val Ser Val Leu Thr Val Leu His Gln Asp Trp Leu
    130                 135                 140
Asn Gly Lys Glu Tyr Lys Cys Lys Val Ser Asn Lys Ala Leu Pro Ala
145                 150                 155                 160
Pro Ile Glu Lys Thr Ile Ser Lys Ala Lys Gly Gln Pro Arg Glu Pro
                165                 170                 175
Gln Val Tyr Thr Leu Pro Pro Ser Arg Asp Glu Leu Thr Lys Asn Gln
            180                 185                 190
Val Ser Leu Thr Cys Leu Val Lys Gly Phe Tyr Pro Ser Asp Ile Ala
        195                 200                 205
```

Val Glu Trp Glu Ser Asn Gly Gln Pro Glu Asn Asn Tyr Lys Thr Thr
    210                 215                 220

Pro Pro Val Leu Asp Ser Asp Gly Ser Phe Phe Leu Tyr Ser Lys Leu
225                 230                 235                 240

Thr Val Asp Lys Ser Arg Trp Gln Gln Gly Asn Val Phe Ser Cys Ser
            245                 250                 255

Val Met His Glu Ala Leu His Asn His Tyr Thr Gln Lys Ser Leu Ser
            260                 265                 270

Leu Ser Pro Gly Lys
        275

<210> SEQ ID NO 12
<211> LENGTH: 846
<212> TYPE: DNA
<213> ORGANISM: Artificial Sequence
<220> FEATURE:
<223> OTHER INFORMATION: Synthesized

<400> SEQUENCE: 12
catatgcacg gtgaaggtac cttcacctct gacctgtcta aacagatgga agaagaagcg      60
gttcgtaaat tcatcgaatg gctgaaaaac ggtggtccgt cttctggtgc cgccgccgcg    120
tctggtggtg gtggttctgg tggtggtggt tctgacaaaa cccacacctg cccgccgtgc    180
ccggcgccgg aactgctggg tggtccgtct gttttcctgt tcccgccgaa accgaaagac    240
accctgatga tctctcgtac cccggaagtt acctgcgttg ttgttgacgt ttctcacgaa    300
gacccggaag ttaaattcaa ctggtacgtt gacggtgttg aagttcacaa cgcgaaaacc    360
aaaccgcgtg aagaacagta caactctacc taccgtgttg tttctgttct gaccgttctg    420
caccaggact ggctgaacgg taagaatac aaatgcaaag tttctaacaa agcgctgccg    480
gcgccgatcg aaaaaaccat ctctaaagcg aaaggtcagc cgcgtgaacc gcaggtttac    540
accctgccgc cgtctcgtga cgaactgacc aaaaaccagg tttctctgac ctgcctggtt    600
aaaggttct accccgtctga catcgcggtt gaatgggaat ctaacggtca gccggaaaac    660
aactacaaaa ccaccccgcc ggttctggac tctgacggtt cttcttcct gtactctaaa    720
ctgaccgttg acaaatctcg ttggcagcag ggtaacgttt tctcttgctc tgttatgcac    780
gaagcgctgc acaaccacta cacccagaaa tctctgtctc tgtctccggg taaataatag    840
aagctt                                                               846

<210> SEQ ID NO 13
<211> LENGTH: 277
<212> TYPE: PRT
<213> ORGANISM: Artificial Sequence
<220> FEATURE:
<223> OTHER INFORMATION: Synthesized

<400> SEQUENCE: 13

Met His Gly Glu Gly Thr Phe Thr Ser Asp Leu Ser Lys Gln Met Glu
1               5                   10                  15

Glu Glu Ala Val Arg Leu Phe Ile Glu Trp Leu Lys Asn Gly Gly Pro
            20                  25                  30

Ser Ser Gly Ala Pro Pro Ser Gly Gly Gly Val Glu Pro Lys
        35                  40                  45

Ser Cys Asp Lys Thr His Thr Cys Pro Pro Cys Pro Ala Pro Glu Leu
    50                  55                  60

Leu Gly Gly Pro Ser Val Phe Leu Phe Pro Pro Lys Pro Lys Asp Thr

Leu Met Ile Ser Arg Thr Pro Glu Val Thr Cys Val Val Val Asp Val
             85                  90                  95

Ser His Glu Asp Pro Glu Val Lys Phe Asn Trp Tyr Val Asp Gly Val
            100                 105                 110

Glu Val His Asn Ala Lys Thr Lys Pro Arg Glu Glu Gln Tyr Asn Ser
            115                 120                 125

Thr Tyr Arg Val Val Ser Val Leu Thr Val Leu His Gln Asp Trp Leu
        130                 135                 140

Asn Gly Lys Glu Tyr Lys Cys Lys Val Ser Asn Lys Ala Leu Pro Ala
145                 150                 155                 160

Pro Ile Glu Lys Thr Ile Ser Lys Ala Lys Gly Gln Pro Arg Glu Pro
                165                 170                 175

Gln Val Tyr Thr Leu Pro Pro Ser Arg Asp Glu Leu Thr Lys Asn Gln
            180                 185                 190

Val Ser Leu Thr Cys Leu Val Lys Gly Phe Tyr Pro Ser Asp Ile Ala
        195                 200                 205

Val Glu Trp Glu Ser Asn Gly Gln Pro Glu Asn Asn Tyr Lys Thr Thr
    210                 215                 220

Pro Pro Val Leu Asp Ser Asp Gly Ser Phe Phe Leu Tyr Ser Lys Leu
225                 230                 235                 240

Thr Val Asp Lys Ser Arg Trp Gln Gln Gly Asn Val Phe Ser Cys Ser
                245                 250                 255

Val Met His Glu Ala Leu His Asn His Tyr Thr Gln Lys Ser Leu Ser
            260                 265                 270

Leu Ser Pro Gly Lys
        275

<210> SEQ ID NO 14
<211> LENGTH: 846
<212> TYPE: DNA
<213> ORGANISM: Artificial Sequence
<220> FEATURE:
<223> OTHER INFORMATION: Synthesized

<400> SEQUENCE: 14
catatgcacg gtgaaggtac cttcacctct gacctgtcta aacagatgga agaagaagcg    60
gttcgtctgt tcatcgaatg gctgaaaaac ggtggtccgt cttctggtgc cgccgccg    120
tctggtggtg gtggtgttga accgaaatct gcgacaaaa cccacacctg cccgccgtgc    180
ccggcgccga aactgctggg tggtccgtct gttttcctgt tcccgccgaa accgaaagac    240
accctgatga tctctcgtac cccggaagtt acctgcgttg ttgttgacgt ttctcacgaa    300
gacccggaag ttaaattcaa ctggtacgtt gacggtgttg aagttcacaa cgcgaaaacc    360
aaaccgcgtg aagaacagta caactctacc taccgtgttg tttctgttct gaccgttctg    420
caccaggact ggctgaacgg taagaatac aaatgcaaag tttctaacaa agcgctgccg    480
gcgccgatcg aaaaaaccat ctctaaagcg aaaggtcagc cgcgtgaacc gcaggtttac    540
accctgccgc cgtctcgtga cgaactgacc aaaaaccagg tttctctgac ctgcctggtt    600
aaaggtttct acccgtctga catcgcggtt gaatgggaat ctaacggtca gccgaaaaac    660
aactacaaaa ccaccccgcc ggttctggac tctgacggtt cttttctcct gtactctaaa    720
ctgaccgttg acaaatctcg ttggcagcag ggtaacgttt tctcttgctc tgttatgcac    780
gaagcgctgc acaaccacta cacccagaaa tctctgtctc tgtctccggg taaataatag    840
aagctt                                                              846

<210> SEQ ID NO 15
<211> LENGTH: 277
<212> TYPE: PRT
<213> ORGANISM: Artificial Sequence
<220> FEATURE:
<223> OTHER INFORMATION: Synthesized

<400> SEQUENCE: 15

Met His Gly Glu Gly Thr Phe Thr Ser Asp Leu Ser Lys Gln Met Glu
 1               5                  10                  15

Glu Glu Ala Val Arg Arg Phe Ile Glu Trp Leu Lys Asn Gly Gly Pro
            20                  25                  30

Ser Ser Gly Ala Pro Pro Pro Ser Gly Gly Gly Ser Gly Gly Gly
        35                  40                  45

Gly Ser Asp Lys Thr His Thr Cys Pro Pro Cys Pro Ala Pro Glu Leu
    50                  55                  60

Leu Gly Gly Pro Ser Val Phe Leu Phe Pro Pro Lys Pro Lys Asp Thr
65                  70                  75                  80

Leu Met Ile Ser Arg Thr Pro Glu Val Thr Cys Val Val Val Asp Val
                85                  90                  95

Ser His Glu Asp Pro Glu Val Lys Phe Asn Trp Tyr Val Asp Gly Val
            100                 105                 110

Glu Val His Asn Ala Lys Thr Lys Pro Arg Glu Glu Gln Tyr Asn Ser
        115                 120                 125

Thr Tyr Arg Val Val Ser Val Leu Thr Val Leu His Gln Asp Trp Leu
    130                 135                 140

Asn Gly Lys Glu Tyr Lys Cys Lys Val Ser Asn Lys Ala Leu Pro Ala
145                 150                 155                 160

Pro Ile Glu Lys Thr Ile Ser Lys Ala Lys Gly Gln Pro Arg Glu Pro
                165                 170                 175

Gln Val Tyr Thr Leu Pro Pro Ser Arg Asp Glu Leu Thr Lys Asn Gln
            180                 185                 190

Val Ser Leu Thr Cys Leu Val Lys Gly Phe Tyr Pro Ser Asp Ile Ala
        195                 200                 205

Val Glu Trp Glu Ser Asn Gly Gln Pro Glu Asn Asn Tyr Lys Thr Thr
    210                 215                 220

Pro Pro Val Leu Asp Ser Asp Gly Ser Phe Phe Leu Tyr Ser Lys Leu
225                 230                 235                 240

Thr Val Asp Lys Ser Arg Trp Gln Gln Gly Asn Val Phe Ser Cys Ser
                245                 250                 255

Val Met His Glu Ala Leu His Asn His Tyr Thr Gln Lys Ser Leu Ser
            260                 265                 270

Leu Ser Pro Gly Lys
        275

<210> SEQ ID NO 16
<211> LENGTH: 277
<212> TYPE: PRT
<213> ORGANISM: Artificial Sequence
<220> FEATURE:
<223> OTHER INFORMATION: Synthesized

<400> SEQUENCE: 16

Met His Gly Glu Gly Thr Phe Thr Ser Asp Leu Ser Lys Gln Met Glu
 1               5                  10                  15

Glu Glu Ala Val Arg His Phe Ile Glu Trp Leu Lys Asn Gly Gly Pro
            20                  25                  30

Ser Ser Gly Ala Pro Pro Ser Gly Gly Gly Ser Gly Gly Gly
        35                  40                  45

Gly Ser Asp Lys Thr His Thr Cys Pro Pro Cys Pro Ala Pro Glu Leu
    50                  55                  60

Leu Gly Gly Pro Ser Val Phe Leu Phe Pro Pro Lys Pro Lys Asp Thr
65                  70                  75                  80

Leu Met Ile Ser Arg Thr Pro Glu Val Thr Cys Val Val Val Asp Val
                85                  90                  95

Ser His Glu Asp Pro Glu Val Lys Phe Asn Trp Tyr Val Asp Gly Val
            100                 105                 110

Glu Val His Asn Ala Lys Thr Lys Pro Arg Glu Glu Gln Tyr Asn Ser
        115                 120                 125

Thr Tyr Arg Val Val Ser Val Leu Thr Val Leu His Gln Asp Trp Leu
    130                 135                 140

Asn Gly Lys Glu Tyr Lys Cys Lys Val Ser Asn Lys Ala Leu Pro Ala
145                 150                 155                 160

Pro Ile Glu Lys Thr Ile Ser Lys Ala Lys Gly Gln Pro Arg Glu Pro
                165                 170                 175

Gln Val Tyr Thr Leu Pro Pro Ser Arg Asp Glu Leu Thr Lys Asn Gln
            180                 185                 190

Val Ser Leu Thr Cys Leu Val Lys Gly Phe Tyr Pro Ser Asp Ile Ala
        195                 200                 205

Val Glu Trp Glu Ser Asn Gly Gln Pro Glu Asn Tyr Lys Thr Thr
    210                 215                 220

Pro Pro Val Leu Asp Ser Asp Gly Ser Phe Phe Leu Tyr Ser Lys Leu
225                 230                 235                 240

Thr Val Asp Lys Ser Arg Trp Gln Gln Gly Asn Val Phe Ser Cys Ser
                245                 250                 255

Val Met His Glu Ala Leu His Asn His Tyr Thr Gln Lys Ser Leu Ser
            260                 265                 270

Leu Ser Pro Gly Lys
        275

<210> SEQ ID NO 17
<211> LENGTH: 43
<212> TYPE: DNA
<213> ORGANISM: Artificial Sequence
<220> FEATURE:
<223> OTHER INFORMATION: Synthesized

<400> SEQUENCE: 17
ggaagaagaa gcggttcgta aattcatcga atggctgaaa aac                    43

<210> SEQ ID NO 18
<211> LENGTH: 43
<212> TYPE: DNA
<213> ORGANISM: Artificial Sequence
<220> FEATURE:
<223> OTHER INFORMATION: Synthesized

<400> SEQUENCE: 18
gtttttcagc cattcgatga atttacgaac cgcttcttct tcc                    43

<210> SEQ ID NO 19
<211> LENGTH: 40
<212> TYPE: DNA

```
<213> ORGANISM: Artificial Sequence
<220> FEATURE:
<223> OTHER INFORMATION: Synthesized

<400> SEQUENCE: 19
agatatacat atgcacggtg aaggtacctt cacctctgac                    40

<210> SEQ ID NO 20
<211> LENGTH: 42
<212> TYPE: DNA
<213> ORGANISM: Artificial Sequence
<220> FEATURE:
<223> OTHER INFORMATION: Synthesized

<400> SEQUENCE: 20
cgtcgacaag cttctattat ttacccggag acagagacag ag                 42
```